US010905520B2

(12) United States Patent
Désaulniers et al.

(10) Patent No.: US 10,905,520 B2
(45) Date of Patent: Feb. 2, 2021

(54) AUTONOMOUS ACCESSORY SUPPORT FOR TRANSPORTING A MEDICAL ACCESSORY

(71) Applicant: Stryker Corporation, Kalamazoo, MI (US)

(72) Inventors: Annie Désaulniers, Bothell, WA (US); William D. Childs, Plainwell, MI (US); Michael Lau, Bristol, IN (US); Connor F. St. John, Kalamazoo, MI (US); Krishna Bhimavarapu, Kalamazoo, MI (US); Christopher R. Sweeney, Portage, MI (US); Joshua E. Mix, Portage, MI (US)

(73) Assignee: Stryker Corporation, Kalamazoo, MI (US)

( * ) Notice: Subject to any disclaimer, the term of this patent is extended or adjusted under 35 U.S.C. 154(b) by 501 days.

(21) Appl. No.: 15/809,438

(22) Filed: Nov. 10, 2017

(65) Prior Publication Data
US 2018/0132966 A1 May 17, 2018

Related U.S. Application Data

(60) Provisional application No. 62/420,894, filed on Nov. 11, 2016.

(51) Int. Cl.
*A61B 90/50* (2016.01)
*G05D 1/00* (2006.01)
(Continued)

(52) U.S. Cl.
CPC ............ *A61B 90/50* (2016.02); *A61B 5/1113* (2013.01); *A61B 5/6891* (2013.01); *A61B 90/98* (2016.02);
(Continued)

(58) Field of Classification Search
CPC .. G05D 1/0088; G05D 1/0225; G05D 1/0274; G05D 1/0242; G05D 1/0255;
(Continued)

(56) References Cited

U.S. PATENT DOCUMENTS 6,183,417 B1 2/2001 Geheb et al.
6,883,201 B2 4/2005 Jones et al.
(Continued)

FOREIGN PATENT DOCUMENTS

AU 2012211373 A1 3/2013
EP 2481388 A1 8/2012
(Continued)

OTHER PUBLICATIONS

Aethon Inc., "Benefits of MedEx" 2017, 1 page.
(Continued)

*Primary Examiner* — Tuan C To
*Assistant Examiner* — Paul A Castro
(74) *Attorney, Agent, or Firm* — Howard & Howard Attorneys PLLC

(57) ABSTRACT

An autonomous accessory support and system for transporting a medical accessory for delivering therapy that is coupled to a patient via a medical line. The autonomous accessory support comprises an accessory post for supporting the medical accessory. A movement module supports the accessory post for moving the accessory post relative to the patient. A tracking module is configured to track movement of the patient or a patient support apparatus relative to the autonomous accessory support and provide a tracking input signal. A controller is in electronic communication with the movement module and the tracking module. The controller controls the movement module to reduce actual patient proximity to a target patient proximity being a distance between the accessory support and the patient or the patient (Continued)

support apparatus sufficient to prevent tensioning of the medical line beyond a tension threshold. The distance may be a selectable preset distance maintained by the controller.

21 Claims, 11 Drawing Sheets

(51) Int. Cl.

| | | |
|---|---|---|
| *G05D 1/12* | (2006.01) | |
| *A61L 2/24* | (2006.01) | |
| *A61L 2/10* | (2006.01) | |
| *G05D 1/02* | (2020.01) | |
| *A61B 5/11* | (2006.01) | |
| *B60L 53/36* | (2019.01) | |
| *A61B 90/98* | (2016.01) | |
| *A61B 5/00* | (2006.01) | |
| *A61M 5/14* | (2006.01) | |
| *A61B 90/00* | (2016.01) | |
| *A61B 5/0205* | (2006.01) | |

(52) U.S. Cl.
CPC .............. *A61L 2/10* (2013.01); *A61L 2/24* (2013.01); *A61M 5/1417* (2013.01); *B60L 53/36* (2019.02); *G05D 1/0088* (2013.01); *G05D 1/028* (2013.01); *G05D 1/12* (2013.01); *A61B 5/0205* (2013.01); *A61B 2090/061* (2016.02); *A61L 2202/11* (2013.01); *A61L 2202/14* (2013.01); *A61L 2202/16* (2013.01); *A61L 2202/25* (2013.01); *A61M 2205/6054* (2013.01); *A61M 2205/6072* (2013.01); *G05D 2201/0206* (2013.01); *Y02T 10/70* (2013.01); *Y02T 10/7072* (2013.01); *Y02T 90/12* (2013.01); *Y02T 90/14* (2013.01); *Y02T 90/16* (2013.01); *Y10S 901/01* (2013.01)

(58) Field of Classification Search
CPC .. G05D 1/0227; G05D 1/0234; G05D 1/0246; G05D 1/0272; G05D 1/028; G05D 1/0219; G05D 1/021; G05D 1/027; G05D 1/0221; G05D 2201/0216; G05D 1/0022; G05D 1/0217; G05D 1/0276; G05D 1/0016; G05D 1/0212; G05D 1/0238; G05D 1/0259; G05D 1/0044; G05D 1/0011; G05D 2201/0206; G05D 1/0257; G05D 1/0251; G05D 2201/02; G05D 1/0094; G05D 2201/0211; G05D 1/02; G05D 1/0055; G05D 1/0077; G05D 1/12; A61B 2090/061; A61B 5/0205; A61B 5/1113; A61B 5/6891; A61B 90/50; A61L 2/24; A61M 2205/6054; A61M 5/1417; B60L 53/36; Y02T 10/7072; Y02T 90/12; Y02T 90/16; Y10S 901/01
See application file for complete search history.

(56) References Cited

U.S. PATENT DOCUMENTS

| | | |
|---|---|---|
| 7,133,746 B2 | 11/2006 | Abramson et al. |
| 7,570,152 B2 | 8/2009 | Smith et al. |
| 7,706,917 B1 | 4/2010 | Chiappetta et al. |
| 7,761,954 B2 | 7/2010 | Ziegler et al. |
| 8,334,779 B2 | 12/2012 | Zerhusen et al. |
| 8,398,408 B1 | 3/2013 | Hansen et al. |
| 8,756,078 B2 | 6/2014 | Collins, Jr. et al. |
| 9,204,823 B2 | 12/2015 | Derenne et al. |
| 9,220,651 B2 | 12/2015 | Hyde et al. |
| 9,404,823 B1 | 8/2016 | Berme et al. |
| 9,569,591 B2 | 2/2017 | Vanderpohl, III |
| 2003/0052787 A1 | 3/2003 | Zerhusen et al. |
| 2007/0129849 A1 | 6/2007 | Zini et al. |
| 2008/0120784 A1 | 5/2008 | Warner et al. |
| 2013/0085625 A1 | 4/2013 | Wolfe et al. |
| 2014/0007664 A1 | 1/2014 | Ito et al. |
| 2014/0080413 A1 | 3/2014 | Hayes et al. |
| 2014/0094990 A1* | 4/2014 | Hyde .................. A61G 1/0281 701/1 |
| 2014/0297327 A1 | 10/2014 | Heil et al. |
| 2015/0088310 A1* | 3/2015 | Pinter .................. B25J 9/1676 700/253 |
| 2015/0139766 A1 | 5/2015 | Cousins |
| 2015/0164599 A1 | 6/2015 | Ross |
| 2016/0367415 A1 | 12/2016 | Hayes et al. |
| 2018/0190100 A1 | 7/2018 | Derenne et al. |

FOREIGN PATENT DOCUMENTS

| | | |
|---|---|---|
| KR | 20130076922 A | 7/2013 |
| WO | 2016172638 A1 | 10/2016 |

OTHER PUBLICATIONS

Aethon Inc., "TUG Robots—Healthcare Benefits", 2017, 5 pages.
Aethon Inc., "TUG—Smart Autonomous Mobile Robot", 2017, 6 pages.
Aethon Inc., "TUG—Autonomous Mobile Robots and Tracking Solutions", 2017, 2 pages.
Apple, Inc., "Apple 85W MagSafe Power Adapter (for 15- and 17-inch MacBook Pro)", www.apple.com, Nov. 2017, 2 pages.
Daily Mail, "RD-D2 Zaps Away Superbugs: Hospital Trials Roving 'Star Wars' Robot that Uses UV Light to Kill Bacteria", www.dailymail.co.uk, Jul. 10, 2014, 4 pages.
Gizbot, "Star Wars-Like Robot to Clean Hospital Rooms", www.gizbot.com, Apr. 15, 2015, 4 pages.
India West, "Star Wars-Like Robot Uses UV Light to Clean Hospitals", www.indiawest.com, Apr. 15, 2015, 2 pages.
Sunrise Golf Carts, "Stewart Golf X9 Follow Golf Cart", www.sunrisegolfcarts.com, 2016, 2 pages.
Wall Street Journal, "Solved: The Case of the Vanishing Drugs: Hi-Tech Tools Help Hospital Pharmacies Manage Inventories and Thwart Employee Drug Theft", Feb. 25, 2014, 1 page.

\* cited by examiner

AUTONOMOUS ACCESSORY SUPPORT FOR TRANSPORTING A MEDICAL ACCESSORY

RELATED APPLICATION

This application claims priority to and the benefit of U.S. Provisional Patent Application No. 62/420,894, filed on Nov. 11, 2016, the entire contents and disclosure of which are hereby incorporated herein by reference.

BACKGROUND

Undergoing medical examination or treatment often requires coupling a medical accessory directly to the body of a patient. A well-known example includes an electrocardiogram (EKG), in which electrodes are placed in contact with the patient's skin to detect the electrical changes caused by the heart's electrophysiologic pattern during each heartbeat. Medical lines (e.g., conductive wires) couple the electrocardiograph with the electrodes affixed to the skin of the patient. Another example includes intravenous (IV) therapy, in which fluids are administered directly into the patient's blood stream. The IV therapy typically infuses fluid therapy from a source (e.g., an IV bag disposed on an IV pole) into the blood stream through a medical line (e.g., IV tube) coupled to a hypodermic needle. Numerous other examples of medical lines coupling a diagnostic or treatment device to the patient are well known to those in the art.

The process to couple a medical line to the patient requires specially trained medical personnel and may be burdensome. For example, electrodes need to be accurately placed on a patient's sternum in order to achieve the desired "leads" for EKG measurement, and a hypodermic needle needs to be accurately placed within a patient's vein to administer IV therapy. Given the resources required to couple a medical line to the patient, limiting the instances in which the patient is decoupled from the medical accessory is an area of particular interest and development.

For any number of reasons, the patient may need to move after the medical line has been coupled to his or her person. Using the above examples, the EKG may detect a cardiac event that requires transporting the patient on a patient support apparatus, such as a hospital bed, to an area of heightened care (e.g., intensive care unit). During transport and thereafter, attending medical providers may desire continuous EKG monitoring to detect deterioration or improvement of the patient's condition. Less seriously, a patient receiving IV saline therapy to restore electrolytes may simply desire to walk across the patient room to use the lavatory. In both scenarios, as well as many others contemplated by the present disclosure, it is desirable for the patient to remain coupled to the diagnostic or treatment device via the medical line during movement of the patient, whether ambulatory or otherwise.

When the patient is moved while coupled to an accessory via a medical line, it readily follows that the accessory needs to be moved as well. For example, an electrocardiograph is typically disposed on a wheeled cart, and a nurse or other medical personnel pushes the wheeled cart within a distance of the patient to provide slack in the medical line. For another example, where the accessory includes an IV bag and IV pole disposed on a wheeled base, the ambulatory patient himself (or medical personnel) pushes or pulls the wheeled base. In many cases, depending on the condition of the patient, moving a mobile medical device or accessory requires a dedicated individual following the patient, or a patient transport apparatus supportably moving the patient must be designed to couple to the medical device or accessory.

Therefore, a need exists in the art for an accessory support designed to overcome one or more of the aforementioned disadvantages.

BRIEF DESCRIPTION OF THE DRAWINGS

Advantages of the present disclosure will be readily appreciated as the same becomes better understood by reference to the following detailed description when considered in connection with the accompanying drawings wherein.

DETAILED DESCRIPTION

Figure 1:
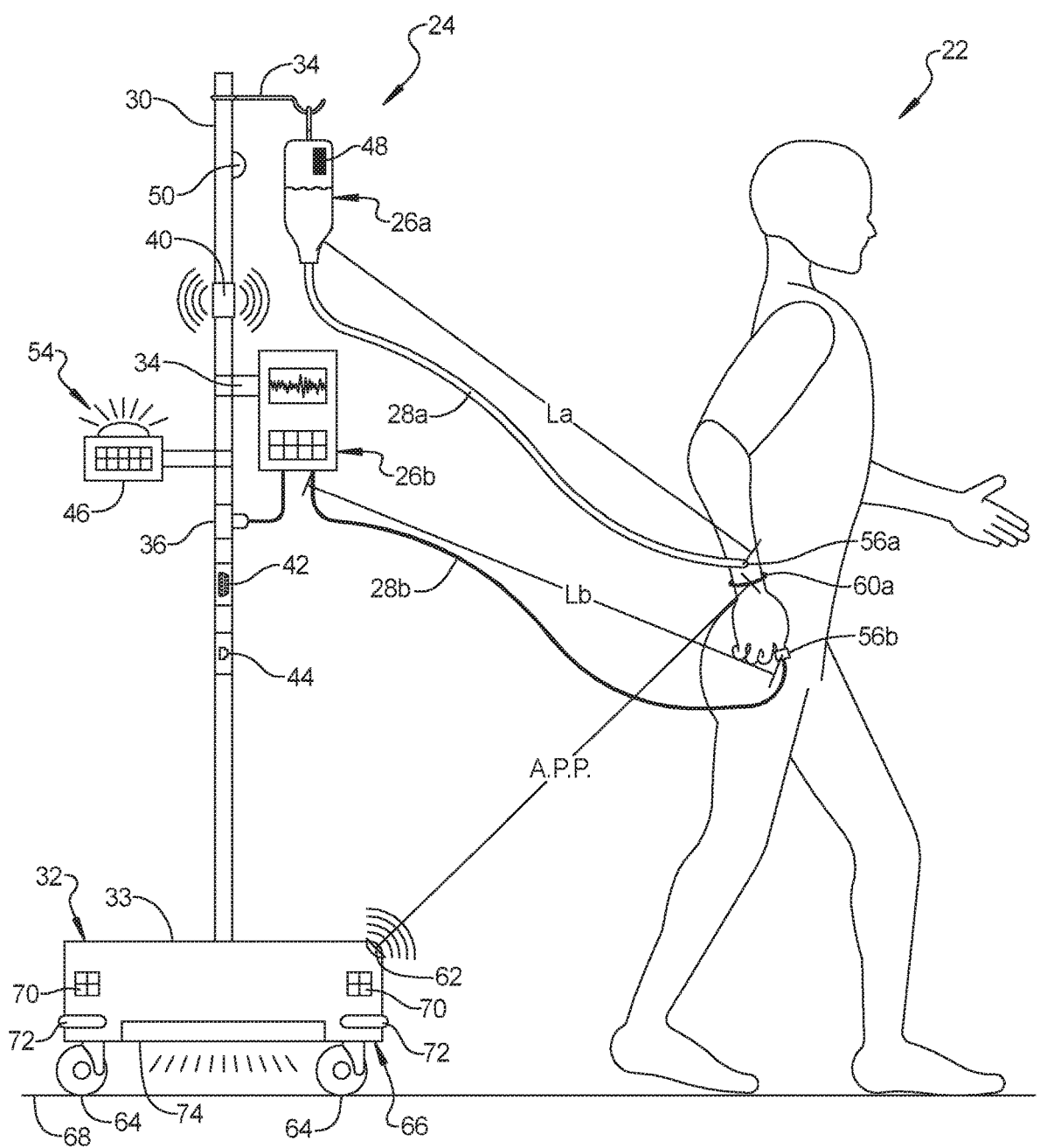
FIG. 1 is an elevational view of an autonomous accessory support in accordance with an exemplary embodiment of the present disclosure, with a patient coupled with medical lines to medical accessories supported by the autonomous accessory support.
Figure 2:
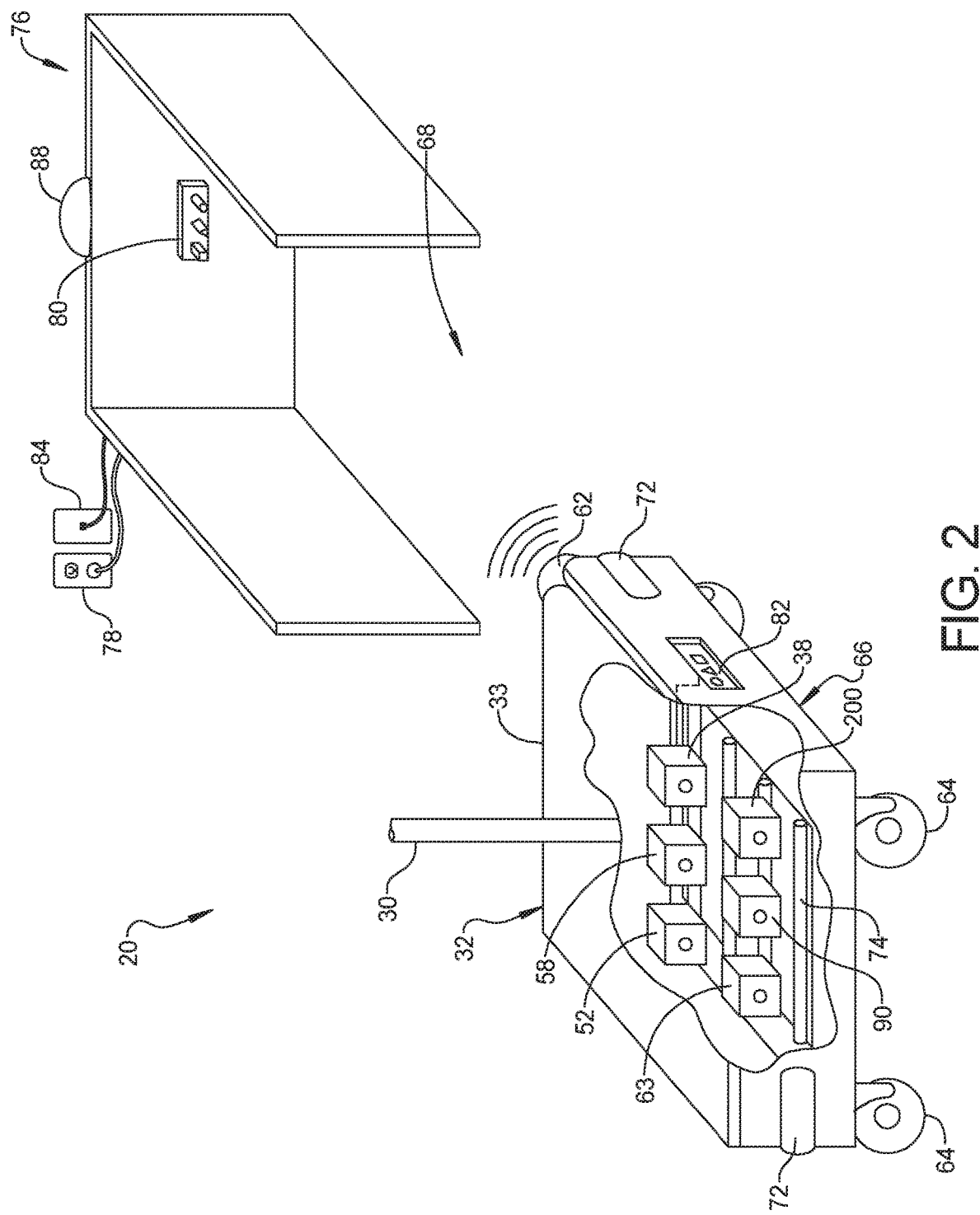
FIG. 2 is a perspective view of an autonomous accessory support system, including schematic representations of electronic components of the autonomous accessory support and a docking station positioned away from the autonomous accessory support.

Referring to FIGS. 1 and 2, an autonomous accessory support system 20 comprises an autonomous accessory support 24 for transporting one or more medical accessories 26a, 26b for medical purposes, such as any device used for patient care, diagnosis, therapy, or surgery. The autonomous accessory support 24 of FIGS. 1 and 2 is an IV pole, but alternatively may comprise any apparatus capable of supporting one or more medical accessories, including a medical stand, a medical computer cart, or an ambulatory assist device, such as a walker. FIG. 1 shows one medical accessory 26a comprising an IV bag for delivering therapy, and another medical accessory 26b comprising a pulse oximetry console for measuring the proportion of oxygenated hemoglobin in the blood as detected by a pulse oximeter coupled to a finger of the patient 22.

Each of the medical accessories 26a, 26b are shown coupled to the patient 22 with a respective medical line 28a, 28b. As used herein, "coupled to the patient" comprises connecting, attaching, joining, linking, securing, tethering, and the like, a component (e.g., pulse oximeter, needle, nasal cannula, etc.) of the medical accessory 26a, 26b, either directly or indirectly, to the patient 22. The coupling is often achieved through mechanical means such as a hypodermic needle penetrating the skin of the patient 22. However, in certain embodiments, the coupling to the patient may also be achieved through other means commonly known in the art, including electromagnetic induction, ultrasound, infrared, radiofrequency, and optical linking. If the medical accessory 26a, 26b is not coupled to the patient 22, the medical accessory 26a, 26b and the patient 22 are considered decoupled.

In a general sense, the medical lines 28a, 28b each have a length sufficient to permit the medical accessories 26a, 26b to be spaced apart from the patient 22 during operation. The medical lines 28a, 28b may be four, five, or ten or more feet in length. Exemplary medical lines may include electrical wiring, medical-grade tubing, and the like. It should be appreciated that the medical lines 28a, 28b may be used to convey electricity, air, oxygen, or any other suitable medium or energy.

The autonomous accessory support 24 comprises an accessory post 30 and a movement module 32 for supporting the medical accessories 26a, 26b. Referring to FIGS. 1 and 2, the illustrated accessory post 30 is an elongated vertical rod. Of course, the shape, size, and configuration of the accessory post is not particularly limited, so long as the accessory post is capable of supporting the medical device(s). In the illustrated embodiment, the accessory post 30 comprises coupling mechanisms 34 that couple the medical accessories 26a, 26b to the accessory post 30. Exemplary coupling mechanisms 34 may include hooks, braces, brackets, loops, pins, and the like.

The accessory post 30 is oriented vertically and extending upwardly from the movement module 32 such that the movement module 32 supports the accessory post 30. The movement module 32 comprises a base 33 and wheels 64. The base 33 comprises a suitable structure within which components of the autonomous accessory support 24 are housed. The wheels 64 are coupled to an underside 66 the base 33 of the movement module 32. The illustrated wheels 64 are casters configured to rotate and swivel relative to the movement module 32 during movement along a floor surface 68. At least one of the wheels 64 is powered and steerable. The remaining wheels 56 may be non-steerable, steerable, non-powered, powered, or combinations thereof. The autonomous accessory support 24 preferably comprises three or four wheels 64 to provide sufficient stability during movement along the floor surface 68, but may include any number of wheels. In other embodiments, the autonomous accessory support 24 may comprise a single spherical wheel.

Figure 4:
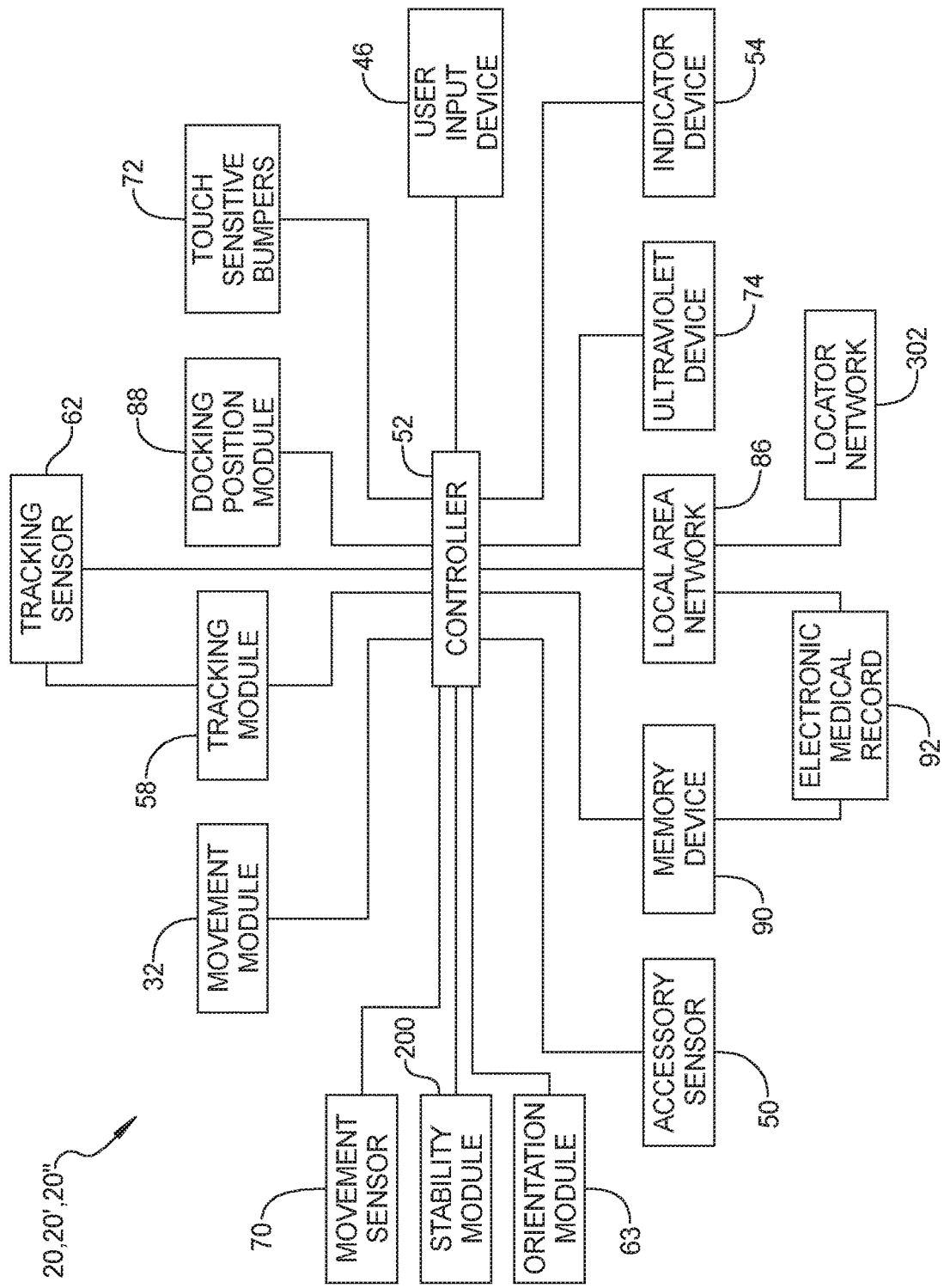
FIG. 4 is a schematic diagram of the autonomous accessory support system in accordance with an exemplary embodiment of the present disclosure.

As disclosed in detail below, the powered and steerable wheel(s) 64 move the movement module 32 in response to a movement output signal from a controller 52 (FIG. 4). The movement module 32 further comprises motors, brakes, electronics and the like, required to operate the autonomous accessory support system 20 in a manner consistent with the objects of present disclosure.

In certain embodiments, with reference to FIG. 2, the autonomous accessory support 24 may include a rechargeable power supply 38. The rechargeable power supply 38 supplies power to the medical accessory 26b electrically coupled to the rechargeable power supply 38 via the accessory port 36. As commonly known in the art, different combinations of electrode materials and electrolytes include lead-acid, nickel cadmium (NiCd), nickel metal hydride (NiMH), lithium ion (Li-ion), and lithium ion polymer (Li-ion polymer). The rechargeable power supply 38 may also power any number of peripheral devices, including a pump, a display, a telephone, and electronic medical equipment.

Referring again to FIG. 1, the accessory post 30 may further comprise a power port 36 that is configured to supply power to the one or more medical accessories 26a, 26b. The power port 36, if present, is configured to couple to one of the medical accessories 26a, 26b that are placed adjacent to, or in contact with, the accessory post 30 to a source of electrical power. Thus, through the power port 36, the accessory post 30 provides sufficient operating power to the medical accessory 26a, 26b coupled thereto. The source of electrical power is not particularly limited, and may be configured to provide direct current or alternating current power to medical accessory 26a, 26b. The power port 36 is in electrical communication with the rechargeable power supply 38. In some instances, the power port 36 comprises an alternating current (AC) power outlet for providing AC power to the medical accessory 26a, 26b. Alternatively, the power port 36 comprises a direct current (DC) connector for providing DC power to the medical accessory 26a, 26b.

Furthermore, it is contemplated that the power port 36 comprises an inductive charging coupler. Thus, when the medical accessory 26a, 26b is positioned adjacent to the power port 36, the medical accessory 26a, 26b receives power from the inductive charging coupler. It is further contemplated that in some instances the power port 36 is configured to provide power for devices other than medical accessories 26a, 26b such as, by way of non-limiting example, cell phones, laptops, tablets, and other portable electronic devices.

The accessory post 30 may further comprise any number of additional components, including but not limited to a wireless antenna 40, a 37-pin connector 42, a data port 44, sensors (e.g., infrared, ultraviolet, touch, proximity, temperature, etc.), a call button, fluid port (not shown), and other input and output ports. The data port 44 allows the medical device coupled thereto to exchange data with the autonomous accessory support 24. By way of non-limiting example, the data port 44 comprises a Universal Serial Bus (USB) interface, an RFID interface, an optical interface, a serial port interface, a High-Definition Multimedia Interface (HDMI), or IEEE 1394 interface. Still other types of data ports are contemplated.

The fluid port allows the medical device coupled thereto to receive fluid from the autonomous accessory support 24, such as one or more medical gases or working gases. The fluid source may be mounted onboard the autonomous accessory support. By way of non-limiting example, the source of fluid is configured to provide at least one fluid selected from the group consisting of a medical gas, a working gas, a liquid for intravenous delivery, a working liquid, and combinations thereof to the medical accessory 26a, 26b.

With continued reference to FIG. 1, the medical lines 28a, 28b are coupled to the patient 22 at patient sites 56a, 56b. For example, in the context of the medical accessory 26a comprising IV therapy, the patient site 56a typically is a forearm of the patient 22 in which the hypodermic needle is inserted. In the context of the medical accessory 26b comprising the pulse oximeter, the patient site 56b typically is a fingertip of the patient 22 to which a sensor device is placed. The medical lines 28a, 28b each have a length La, Lb defined between an end coupled to the patient site 56a, 56b and an opposite end coupled to the medical accessory 26a, 26b, as illustrated in FIG. 1, which is supported by the autonomous accessory support 24.

An object and advantage of the autonomous accessory support system 20 comprises moving the autonomous accessory support 24 in an autonomous manner so as to prevent tensioning of the medical lines 28a, 28b as a position of the patient 22 changes relative to autonomous accessory support 24, and the supported medical devices. In a general sense, tensioning of the medical lines 28a, 28b comprises being in a strained state or condition resulting from forces acting in opposition to each other, particularly the forces from the opposite ends of the medical lines 28a, 28b coupled to the medical accessory 26a, 26b and the patient 22. Among other advantages, the autonomous accessory support 24 maintains a distance between the patient 22 and the medical accessory 26a, 26b less than the length La, Lb of the medical lines 28a, 28b. Providing slack and preventing tensioning of the medical lines 28a, 28b is desired in some embodiments to prevent discomfort or pain due to pulling of the medical lines 28a, 28b at the patient site 56a, 56b, and to avoid decoupling of the medical accessory 26a, 26b from the patient 22. Those having skill in the art appreciate that the catenary of the medical lines 28a, 28b results in some amount of tension. As described below, the autonomous accessory support 24, at a minimum, prevents tensioning sufficient to decouple the medical line 28a, 28b from the patient 22. The present disclosure contemplates some tension in the medical lines 28a, 28b may be tolerated due to catenary or otherwise.

The position or movement of the patient 22 is tracked to determine the heading of the autonomous accessory support 24. To do so, in an autonomous manner, the autonomous accessory support 24 comprises a tracking module 58 (see FIGS. 2 and 4) configured to track the position or movement of the patient 22 relative to the autonomous accessory support 24 and provide a tracking input signal. A controller 52 is in electronic communication with the movement module 32 and the tracking module 58.

In one embodiment, the tracking module 58 comprises a tracking sensor 62 configured to detect a position of the patient 22, which may be used to determine the distance and direction that the patient is traveling. FIG. 1 shows the tracking sensor 62 coupled to the base 33 of the movement module 32. Additionally or alternatively, one or more tracking sensors 62 may be coupled to the accessory post 30, the movement module 32, or any suitable structure of the autonomous accessory support 24. The tracking sensor 62 may comprise an optical, acoustic, radio and/or infrared sensor configured to detect the patient 22 with or without a discrete tracking device 60a, 60b (FIGS. 1 and 5) coupled to the patient 22, a caregiver, patient support apparatus 100, and/or other moving object or person. Alternatively, a tracking sensor may be associated with the patient 22 and configured to detect a discrete tracking device coupled to the accessory post 30, the movement module 32, or any suitable structure of the autonomous accessory support 24.

The controller 58 and the tracking sensor 62 determine a distance and direction of the patient 22 relative to the tracking sensor 62. The distance may be a distance magnitude of a straight line extending between the tracking sensor 62 and the patient 22. The direction may be an angular displacement relative to a reference orientation determined by an orientation module 63, which is discussed in detail below. Based on the position of the patient 22 relative to the tracking sensor 62, the tracking module 58 provides the tracking input signal to the controller 52. In another example, the tracking module 58 determines a vector or other spatial relationship (e.g., Cartesian coordinates) of the tracking device 60a relative to the ambulatory accessory support 24 as measured by the tracking sensor 62. The position may be tracked iteratively, discretely, or in a continuous manner to track the movement of the patient 22 relative to the tracking sensor 62.

The present disclosure also contemplates the tracking module 58 may correlate the position of the patient 22 relative to the base 33 of the movement module 32, the accessory post 30, the medical accessory 26a, 26b, or any other suitable structure or reference point of the autonomous accessory support 24. The position of the structure or reference point relative to the tracking sensor 62 is known and may be programmed or otherwise incorporated into the tracking module 58. The tracking input signal provided to the controller 52 may comprise the position of the patient 22 as modified to reflect the position of the patient 22 relative to the desired structure or reference point. In one example, the tracking input signal comprises the position of the patient 22 relative to the accessory post 30.

To facilitate tracking the movement of the patient 22, a tracking device 60a may be coupled to the patient 22. The tracking device 60a may be an electronic tag or beacon configured to be detected by the tracking sensor 62. In some examples, the tracking device 60a is a passive radiofrequency identification (RFID) tag, active RFID tag, electromagnetic tag, acousto-magnetic tag, microwave tag, and the like. For example, FIG. 1 shows the patient 22 wearing the tracking device 60a comprising a bracelet having a passive RFID tag. Alternatively or additionally, the tracking device 60a may be attached to or integrated within a patient gown or other article of clothing, or otherwise coupled to the patient in any suitable manner. As mentioned, the tracking device 60a may be coupled to the caregiver, or another moving object or person.

Figure 9:
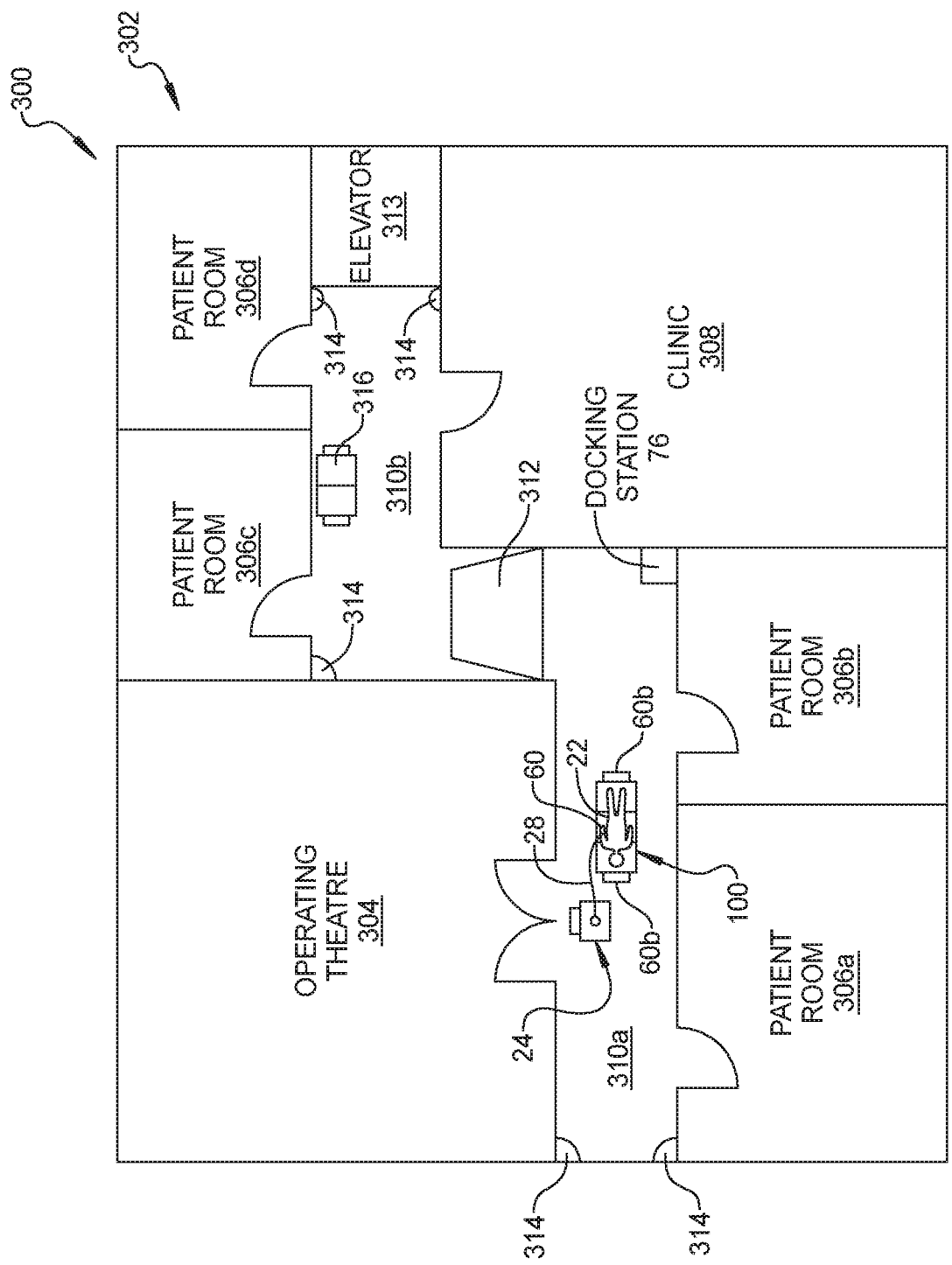
FIG. 9 is a schematic diagram of a medical facility, with the autonomous accessory support, docking station, and patient support apparatus depicted on a medical floor of the medical facility.

In another exemplary embodiment and with reference to FIG. 9, a locator network 302 within a medical facility 300 is configured to track the patient 22 and/or the patient support apparatus 100 and the position of the autonomous accessory support 24. The locator network 302 may comprise a plurality of sensors 314. The sensors 314 of the locator network 302 may be optical, infrared, sonographic, or any other suitable detection-based technology configured to wirelessly detect a device at a distance. Typically, the sensors 314 are mounted to walls and/or the ceiling within corridors 310a, 310b of the medical facility 300. The sensors 314 may be configured to detect the tracking device 60a coupled to the patient 22 and/or the tracking devices 60b coupled to the patient support apparatus 100. Further, the sensors 314 may be configured to detect the tracking module 58 of the autonomous accessory support 24. To that end, the tracking module 58 may comprise a transmission device coupled to the autonomous accessory support 24. The transmission device comprises, for example, a passive RFID tag, active RFID tag, electromagnetic tag, acousto-magnetic tag, microwave tag, Wi-Fi card, or other suitable detection means as commonly known in the art. Another exemplary system to track the patient 22 and/or the patient support apparatus 100 is disclosed in commonly owned U.S. Pat. No. 9,204,823 to Derenne et al., which is herein incorporated by reference in its entirety.

The tracking module 58 of the autonomous accessory support 24 may be configured to transmit signals to and/or receive signals from the locator network 302. In one embodiment, the locator 302 network transmits to the tracking module 58 the positions of the patient 22 and/or the patient support apparatus 100 and the position of the autonomous accessory support 24. The controller 52 receives from the tracking module 58 a first location input signal based on a location of the tracking device 60a, 60b. Further, the controller 52 is configured to receive a second location input based on a location of the tracking module 58. In one example, the sensors 314 effectively "triangulates" the locations of each of the tracking device 60a, 60b and the tracking module 58. Based on the first location input and the second location input, the tracking module 58 is configured to determine the tracking input signal. Additional exemplary systems and methods for tracking are disclosed in commonly owned U.S. Patent Application Pub. No. 2016/0367415, filed on Jun. 17, 2016, which is herein incorporated by reference in its entirety.

Referring now to FIGS. 2 and 4, the controller 52 is in electronic communication with the movement module 32 and the tracking module 58. The controller 52 is configured to perform any number of electronic functions of the autonomous accessory support system 20.

In one embodiment, the controller 52 is configured to determine a target patient proximity. The target patient proximity is a distance between the autonomous accessory support 24 and the patient 22 sufficient to prevent tensioning of the medical line 28 beyond a tension threshold. The tension threshold may be defined as a lack of slack in the medical line 28a, 28b such that the patient 22 experiences pulling at the patient site 56a, 56b by the medical line 28a, 28b. At a minimum, the tension threshold comprises an amount of tensioning sufficient to decouple the medical line 28a, 28b from the patient 22. Thus, in a general sense, the target patient proximity may be based, at least in part, on the length La, Lb of the medical line 28a, 28b. If more than one medical line 28a, 28b is coupled to the patient 22, such as the example illustrated in FIG. 1, the target patient proximity is based on the length La, Lb of the shorter of the medical lines 28a, 28b to prevent tensioning of the shorter medical line 28a, 28b beyond the tension threshold.

In at least some examples of the present disclosure, the target patient proximity is manually entered by the user. A user input 46 (FIG. 1) may be coupled to the accessory post 30 and configured to receive an input of a user (e.g., patient, caregiver, medical professional, etc.). The length La, Lb of the medical line 28 may be known and provided to the controller 52 by a user via the user input device 46. In such an example, the tracking device 60a is preferably coupled to the patient 22 reasonably proximate to the patient site 56a, 56b to best approximate the length La, Lb of the medical line 28a, 28b. In other examples, the tracking sensor 62 detects an initial position of the tracking device 60a coupled to the patient 22 when the medical line 28a, 28b has suitable slack. Based on the initial position, the controller 52 approximates or determines the target patient proximity (between the autonomous accessory support 24 and the patient 22) sufficient to prevent tensioning of the medical line 28a, 28b beyond the tension threshold.

The controller 52 is further configured to determine an actual patient proximity. Referring to FIG. 1, the actual patient proximity, or APP, is a distance magnitude between the patient 22 and the autonomous accessory support 24. More specifically, the APP is the distance magnitude between the patient 22 and the tracking module 58 (i.e., the tracking sensor 62 or other reference structure or point). Since the tracking module 58 tracks the position of the patient 22 and provides the tracking input signal to the controller 52, the APP is based, at least in part, on the tracking input signal. The APP may be provided to the controller 52 from the tracking module 58 either continuously or intermittently, and typically changes as the patient 22 moves relative to the autonomous accessory support 24. Thus, the tracking module 58 continuously provides the tracking input signal based on tracked movement, and the controller 52 may continuously determine the actual patient proximity based on the tracking input signal.

As is most often the case, if the patient 22 is moving away from the autonomous accessory support 24, the actual patient proximity would be expected to increase. In some instances, the autonomous accessory support 24 is initially stationary as the patient 22 moves away; and in other instances, the autonomous accessory support 24 is moving along with the patient 22. At some moment in both instances, the movement of the patient 22 causes the actual patient proximity to exceed the target patient proximity. The controller 52 is further configured to determine a movement output signal based on the target patient proximity and the actual patient proximity. The movement output signal, in a general sense, comprises a vector—a magnitude and a direction in which the autonomous accessory support 24 must move in order to reduce the actual patient proximity to the target patient proximity. Often, the directional component of the movement output signal comprises the movement just performed by the patient 22 as determined by the tracking module 58, or some offset thereof, such that the autonomous accessory support 24 effectively follows the path of the patient 22. The magnitude of the movement output signal may be a time interval change in position (i.e., speed) of the patient 22 relative to the autonomous accessory support 24 in order to match the speed of the autonomous accessory support 24 to that of the patient 22. Should the actual patient proximity not exceed the target proximity, the controller 52 may provide a no movement output signal at that particular instant. The movement output signal is transmitted to the movement module 32 to reduce the actual patient proximity to the target proximity. The movement of the autonomous accessory support 24 is facilitated by one or more of the powered and steerable wheels 64.

Figure 5:
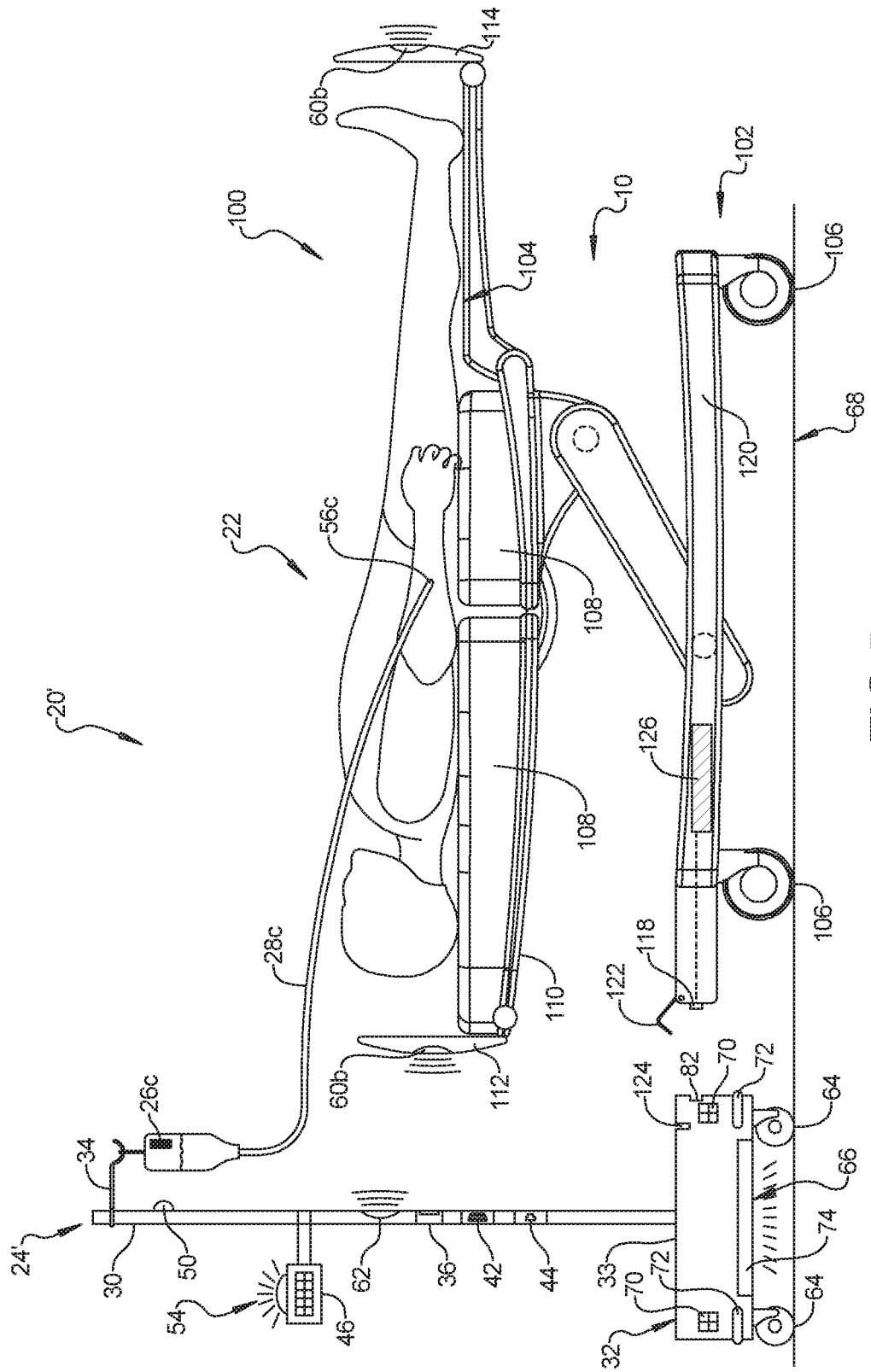
FIG. 5 is an elevational view of an autonomous accessory support system in accordance with another exemplary embodiment of the present disclosure, with the patient supported by a patient support apparatus, the patient being coupled with a medical line to a medical accessory supported by the autonomous accessory support.

In many instances, the patient 22 does not ambulate but is rather bedbound when moved within the medical facility. FIG. 5 shows a system 20' for transporting a medical accessory 26c coupled to the patient 22 with the medical line 28c in accordance with another exemplary embodiment of the present disclosure. The system 20' comprises the patient support apparatus 100 configured to transport and support the patient 22 coupled to the medical accessory 26c via the medical line 28c at a patient site 56c. The patient support apparatus 100 illustrated in FIG. 5 is a hospital bed, but alternatively may be a stretcher, cot, or similar support apparatus without deviating from the objects of the present disclosure. Furthermore, the autonomous accessory support system 20, 20' may be implemented with a patient 22 using a walker, rollator, or other ambulatory assist device, or a wheelchair, ambulance cot, or other patient transport device.

With continued reference to FIG. 5, the patient support apparatus 100 comprises a base 102 and a patient support surface 104 supported by the base 102. The base 102 is configured to rest upon the floor surface 68 and support and stabilize the patient support apparatus 100. The base 102 comprises wheels 106 configured to facilitate transport over the floor surface 68. The construction of the base 102 may take on any known or conventional design, and is not limited to that specifically set forth in FIG. 5. A mattress 108 is disposed on a patient support deck 110 supported by the base 102. A headboard 112 and a footboard 114 may be coupled at opposite ends of the patient support deck 110 as shown. FIG. 5 shows the patient 22 in the supine position on the mattress 108 comprising the patient support surface 104.

The system 20' further comprises an autonomous accessory support 24'. The autonomous accessory support 24' comprises the accessory post 30 for supporting the medical accessory 26c, and the movement module 32 supporting the accessory post 30 for moving the autonomous accessory support 24 relative to the patient 22. In many respects, the autonomous accessory support 24' of FIG. 5 is similar to the autonomous accessory support 24 of FIG. 1.

Like the autonomous accessory support 24 of FIG. 1, the autonomous accessory support 24' includes a tracking module 58 configured to track movement of the patient 22 or the patient support apparatus 100 relative to the autonomous accessory support 24' and provide the tracking input signal.

The movement of the patient 22 or the patient support apparatus 100 is tracked relative to the movement module 32, the accessory post 30, the medical accessory 26c, or any other suitable structure or reference point of the autonomous accessory support 24. To facilitate tracking the patient support apparatus 100, tracking devices 60b may be coupled to the patient support apparatus 100. The patient support apparatus 100 of FIG. 5 shows a tracking device 60b coupled to each of the headboard 112 and the footboard 114. Since the patient support apparatus 100 typically moves longitudinally by pushing or pulling the headboard 112 or the footboard 114, coupling the tracking devices 60b to the headboard 112 and the footboard 114 may provide improved detection by the tracking sensor 62 of the autonomous accessory support 24', which typically follows the path (or an offset thereof) of the patient support apparatus 100, as previously disclosed herein. Other suitable locations for operably coupling the tracking devices 60b may include the base 102, the patient support deck 110, an elongated frame member 120, side rails (not shown), and the like.

FIG. 5 shows the tracking sensor 62 coupled to the accessory post 30 at an elevation generally commensurate with the tracking devices 60b of the patient support apparatus 100. The tracking module 58 may comprise optical, acoustic, and/or infrared sensors configured to detect the patient support apparatus 100. Furthermore, the present disclosure contemplates that the tracking device 60a (e.g., bracelet with passive RFID tag) may also be coupled to the patient 22 while positioned on the patient support apparatus 100, and the tracking sensor 62 detects each of the tracking devices 60a, 60b.

The system 20' further comprises the controller 52 in electronic communication with the movement module 32 and the tracking module 58. The controller 52 is configured to control the movement module 32 to maintain a preset distance between the patient support apparatus 100 and the medical accessory 26c based on the tracking input signal. Additionally or alternatively to maintaining a preset distance between the patient support apparatus 100 and the medical accessory 26c, the controller 52 may be configured to maintain positioning between the autonomous accessory support 24 and the patient support apparatus 100 to avoid tensioning the medical line 28c beyond a tension threshold consistent with the disclosure described herein. In doing so, the controller is configured to determine and transmit the movement output signal to reduce the actual patient proximity to the target patient proximity between the patient support apparatus 100 and the medical accessory 26c based on the tracking input signal.

The preset distance may be selectable by the user. To that end, the system 20' further comprises the user input device 46 configured to provide a user input signal to the controller 52. The user input device 46 may be coupled to the autonomous accessory support 24', or positioned away from the same. FIG. 5 shows the user input devices 46 comprising a tactile or touch-sensitive keypad coupled to the accessory post 30 similar to FIG. 1. The present disclosure contemplates that the user input device 46 may also comprise a mobile device such as a smartphone, personal digital assistance, tablet, and the like.

Additionally or alternatively to the user selecting the preset distance, the user input signal may be based on other input parameters to the user input device 46. For example, the user may input a user-selected tension threshold in the medical lines 28a, 28b, 28c. The tension in each of the medical lines 28a, 28b, 28c is monitored by a sensor (e.g., strain gauge) and the controller 52 controls the movement module 32 to maintain the distance between the patient 22 and the medical accessory 26a, 26b, 26c such that the user-selected tension threshold is not exceeded. In another example, the user inputs or selects on the input device 46 a model number of known medical lines stored in a database. Based on the inputted or selected model numbers, the controller 52 determines the preset distance and control the movement module 32 to maintain the preset distance between the patient 22 and the medical accessory 26a, 26b, 26c.

Based on the user input signal provided by the user input device 46, either from numerical distance input, numerical user-selected tension threshold, or model number input or selection, the controller 52 is configured to adjust the preset distance. Typically, the preset distance is smaller than or less than the length of the medical line 28c so as to provide slack and prevent tensioning of the medical line 28c, which could otherwise result in decoupling of the medical accessory 26c from the patient 22.

It is contemplated that the selectable preset distance may be incorporated into the exemplary embodiment of FIG. 1. The controller 52 may be configured to control the movement module 32 to maintain the preset distance between the patient 22 and the medical accessory 26a, 26b based on the tracking input signal. The preset distance is generally selected so as to prevent tensioning of the medical line 28a, 28b at the patient sites 56a, 56b.

Referring back to FIG. 5, the patient support apparatus 100 may further comprise a docking port 118 coupled to the base 102. With concurrent reference to FIG. 2, the autonomous accessory support 24' further comprises the rechargeable power supply 38 coupled to the movement module 32. The rechargeable power supply 38 comprises a charging port 82, as described in detail below. The docking port 60b is configured to be removably coupled and supply power to the charging port 82 of the autonomous accessory support 24'. The present disclosure also contemplates the docking port

60b may be coupled to the patient support deck 110, the headboard 112, and/or the footboard 114.

The docking port 118 may be coupled to an elongated frame member 120 of the base 102, as illustrated in FIG. 5. A second, third, or fourth docking port 118 may be coupled to remaining ends of the elongated frame member 120 of the base 102 to provide additional versatility in quickly coupling the autonomous accessory support 24' to the patient support apparatus 100. A docking coupler 122 may be coupled to the base 102 proximate the docking port 118. The docking coupler 122 removably couples with an accessory support coupler 124 of the autonomous accessory support 24'. The accessory support coupler 124 is coupled to the movement module 32 or any other suitable structure of the autonomous accessory support 24'. In the exemplary embodiment of FIG. 5, the docking coupler 122 is a pivoting member with a flanged end configured to interlock with a slot-like recess of the accessory support coupler 124. Of course, any suitable configuration of the docking coupler 122 and accessory support coupler 124 is contemplated, such as a magnetic coupler.

When the docking coupler 122 and the accessory support coupler 124 are coupled, defining a coupled configuration of the patient support apparatus 100 and the autonomous accessory support 24', the charging port 82 and the docking port 60b remain engaged regardless of movement of one of the autonomous accessory support 24' and the patient support apparatus 100. In other words, in the coupled configuration the horizontal relative movement between the autonomous accessory support 24' and the patient support apparatus 100 is fixed.

The patient support apparatus 100 may further comprise a power supply 126. The power supply 126 is in electrical communication with the docking port 118 such that, in the coupled configuration, the power supply 126 supplies power to the autonomous accessory support 24'. The supplied power may power the immediate operation of the autonomous accessory support 24' to preserve the rechargeable power supply 38, and/or charge the rechargeable power supply 38.

Figure 6:
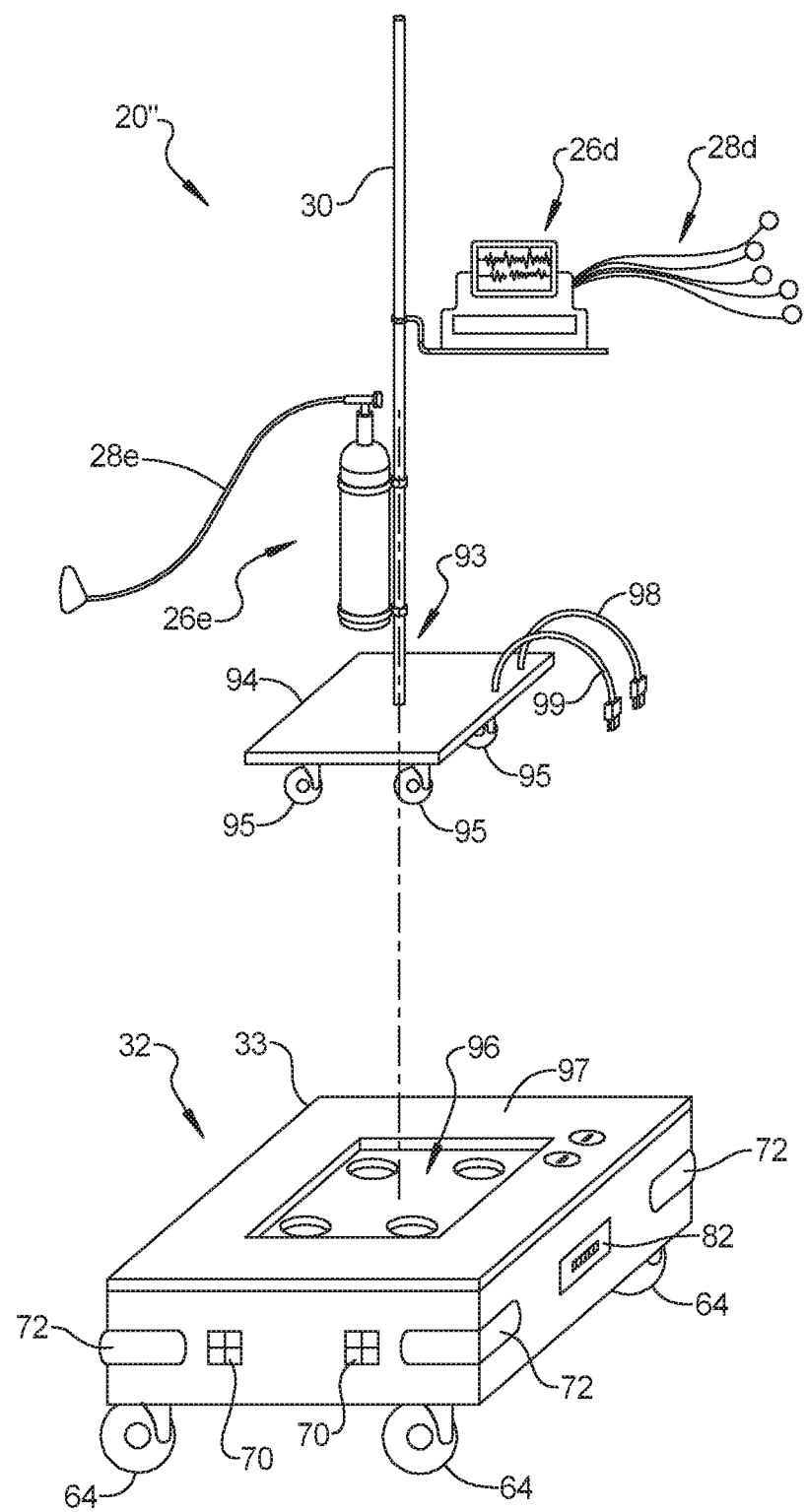
FIG. 6 is a perspective view of an autonomous accessory support in accordance with another exemplary embodiment the present disclosure, with a conventional IV pole removably coupled to a movement module.

Referring to FIG. 6, an autonomous accessory support system 20" in accordance with another exemplary embodiment of the present disclosure is illustrated. Similar to previous embodiments disclosed herein, the autonomous accessory support system 20" comprises the movement module 32 having wheels 64 configured to move over a surface.

In many respects the accessory post 30 and a support frame 94 comprise a conventional IV pole commonly known in the art. The accessory port 30 supports the medical accessory 26d, 26e. For exemplary purposes, the medical accessories 26d, 26e of FIG. 6 comprise an EKG machine and an oxygen tank. Each of the medical accessories 26d, 26e are configured to be coupled to the patient via the medical lines 28d, 28e. The accessory post 30 further comprises a bottom portion 93, and the support frame 94 is coupled to the bottom portion 93 of the accessory post 30. The support frame 94 comprises wheels 95, typically non-powered casters, such that the accessory post 30 and support frame 96 slidably move about the floor surface 68 under the force of the user.

In the autonomous accessory support system 20" of FIG. 6, the support frame 94 is configured to be removably coupled to and supported by the movement module 32, and more specifically the base 33 of the movement module 32, after which the autonomous accessory support system 20" operates as previously described herein. One exemplary manner in which the support frame 94 is removably coupled to and supported by the movement module 32 comprises a cavity 96 within an upper surface 97 of the base 33 of the movement module 32 sized and shaped to receive the support frame 94, as illustrated in FIG. 6. Lowering the support frame 94 to within the cavity 96 couples the support frame 94 and the base 33 of the movement module 32 without additional fastening means. Relative stability is ensured by the counterpoising shapes of the cavity 96 and the support frame 94. Among other advantages, the autonomous accessory support system 20" provides for quickly and easily converting conventional IV poles into the autonomous accessory support system disclosed herein. Power connections 98 and data connections 99 may also be provided.

Referring to FIG. 2, the autonomous accessory support system 20, 20', 20" may further comprise a docking station 76 separate from the patient support apparatus 100. The autonomous accessory support 24 removably couples to the docking station 76. The docking station 76 is in electrical communication with a power source 78, typically a common electrical outlet. The docking station 76 comprises the docking port 80. The rechargeable power supply 38 coupled to the movement module 32 comprises a charging port 82. The docking port 80 is configured to removably couple and supply power to the charging port 82 of the autonomous accessory support 24. More specifically, the coupling of the docking port 80 and the charging port 82 permits the docking station 76 to supply power to the autonomous accessory support 24, and more particularly to recharge the rechargeable power supply 38 of the autonomous accessory support 24.

Furthermore, the docking station 76 may be in electrical communication with a data port 84 such as an Ethernet port. The data port 84 may be in electronic communication with a Local Area Network (LAN) 86 (FIG. 4) associated with the medical facility. Other types of computer networks are contemplated without deviating from the objects of the present disclosure. The coupling of the docking port 80 and the charging port 82 may also provide for data transmission between the autonomous accessory support 24 and the LAN 86, which will be discussed in greater detail below. Alternatively or additionally, the docking station 76 transmits data to and receives data from the LAN 86 wirelessly via the wireless antenna 40 or through other wireless means commonly known in the art.

The docking station 76 typically rests on the floor surface 68 such that the autonomous accessory support 24 docks with the docking station 76. More specifically, docking generally comprises positioning the base 33 of the movement module 32 of the autonomous accessory support 24 adjacent the docking station 76 and coupling the docking port 80 and the charging port 82. In the illustrated docking station 76 of FIG. 2 comprising a generally U-shaped structure, docking further comprises at least partially recessing the base 33 of the movement module 32 of the autonomous accessory support 24 within the structure of the docking station 76.

Figure 3:
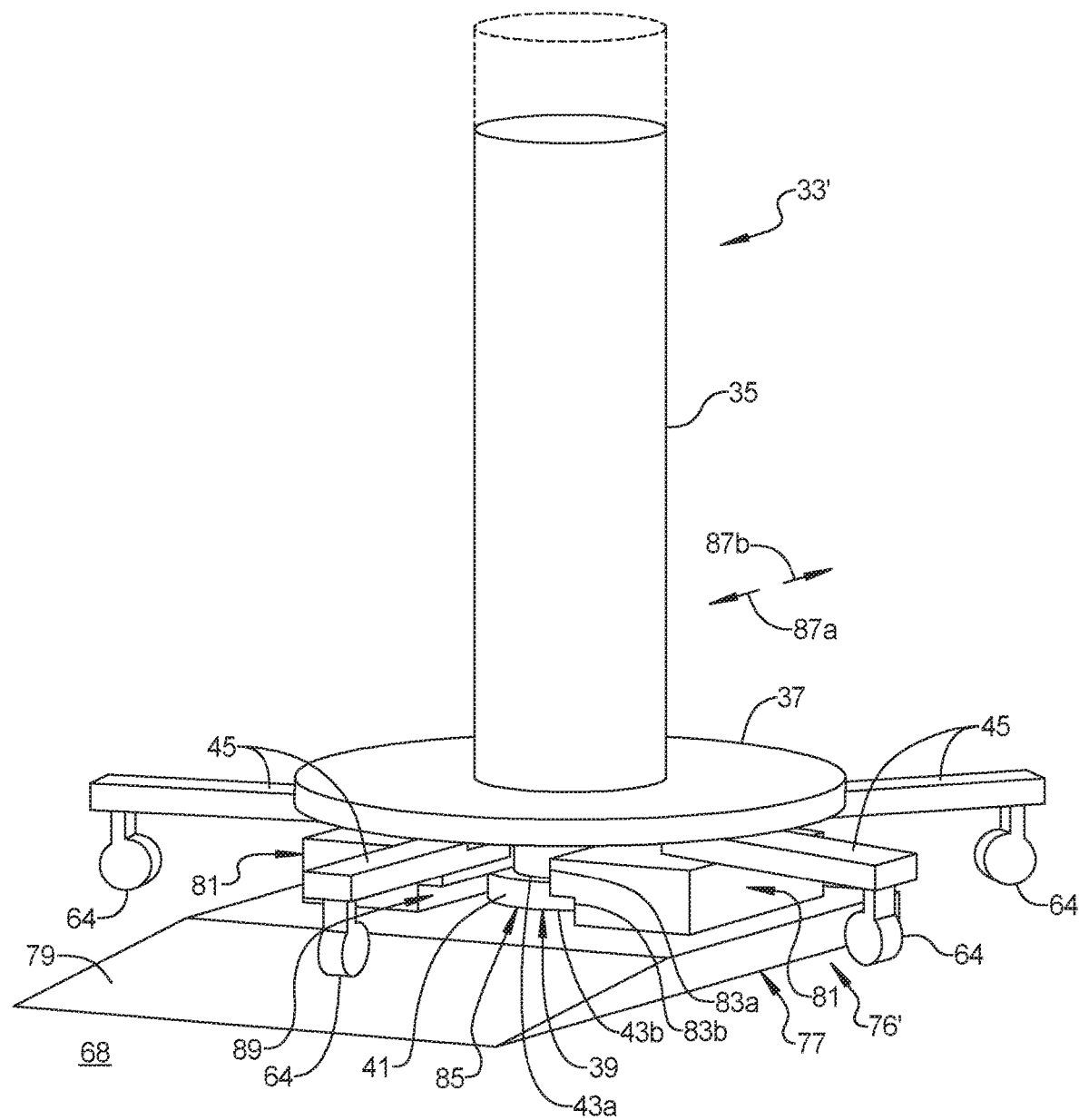
FIG. 3 is a perspective view of a base of an autonomous accessory support system coupled with a docking station.

FIG. 3 shows an alternative docking station 76' and a base 33' in accordance with another exemplary embodiment of the present disclosure. The base 33' comprises a tubular member 35 oriented vertically and having one end fixedly coupled to a base coupler 37. The base coupler 37 of FIG. 3 is a disc-shaped member and positioned coaxially with the tubular member 35. The tubular member 35 may comprise a portion of the accessory post 30 of the present disclosure, and/or the accessory post 30 may be disposed atop and/or operably coupled to the tubular member 35.

The base 33' of the movement module 32 comprises a base connector 39 configured to operably couple with the docking station 76', as described below. The base connector 39 is coupled to the tubular member 35, the base coupler 37, or any other suitable structure of the base 33'. The base connector 39 is of any suitable size and shape to operably couple to the docking station 76. In one exemplary embodiment illustrated in FIG. 3, the base connector 39 comprises a cylindrical structure having a narrower intermediate portion 43a and a wider terminal portion 43b. FIG. 3 shows the base connector 39 positioned coaxially with the tubular member 35 and the base coupler 37, but other suitable configurations and constructions are contemplated.

A plurality of legs 45 may extend radially from the base 33 as illustrated in FIG. 3. When viewed in plan, the legs 45 of FIG. 3 form a star-like configuration. The illustrated embodiment includes five legs (one hidden), but any number of legs may be provided. The legs 45 may be coupled to an underside of the base coupler 37, and/or to the tubular member 35 or the base connector 39. Wheels 64 are coupled to each of the legs 45 of the base 33' of the movement module 32. The wheels 64 may be casters configured to rotate and swivel relative to the movement module 32 during movement along the floor surface 68. At least one of the wheels 64 is powered and steerable. The remaining wheels 56 may be non-steerable, steerable, non-powered, powered, or combinations thereof.

The docking station 76' of FIG. 3 comprises a base portion 77 configured to rest on the floor surface 68. The base portion 77 may comprise an incline 79 to provide a smooth transition from the floor surface 68 for one or more of the wheels 64 of the base 33'. Additionally or alternatively, the legs 45 of the base 33' may be designed such that no incline 79 is necessary. For example, the legs 45 may be radially spaced apart from one another in a manner such that the wheels 64 avoid the docking station 76' when the base 33' docks with the docking station 76', as illustrated in FIG. 3. In such an embodiment, the footprint of the base portion 77 is correspondingly minimized.

The docking station 76' comprises one or more docking barriers 81. The docking barrier 81 is a structure extending upwardly from the base portion 77. As shown in FIG. 3, the docking barrier 81 comprises a slotted portion 83b configured to receive the terminal portion 43b of the base connector 39, and a protruded portion 83a configured to receive the intermediate portion 43a of the base connector. The protruded portion 83a and the slotted portion 83b define a cavity 85 within which the base connector 39 is disposed during docking of the base 33' with the docking station 76'. When disposed within the cavity 85, the terminal portion 43b of the base connector 39 may be wider than the slotted portion 83b of the docking barrier 81 such that the base 33' is constrained from moving upwardly relative to the floor surface 48.

The docking barrier 81 may comprise a pair of barriers disposed on opposing sides of the cavity 85. In other words, the cavity 85 may extend between the pair of barriers such that the base connector 39 may dock or undock from either one of two ends of the cavity 85. With reference to FIG. 3, the base 33' may undock by moving in the direction of arrow 87a and/or arrow 87b. A second inline (not shown) may be included to provide a smooth transition to the floor surface in the direction of arrow 87b. In another exemplary embodiment, the docking barrier 81 may comprise three barriers forming a generally U-shaped barriers. In such a configuration, the base 33' can undock only by moving in the direction of arrow 87a. The configuration may be suited for the docking station 76' being positioned adjacent a wall of the medical facility or other operating environment. In still another example, the docking station 76' is substantially star-shaped (when viewed in plan) such that the base 33' may approach and dock from any direction.

The base connector 39 may comprise a charging port 41. The charging port 41 may be a male or female connector similar to the charging port 82 previously disclosed herein. Likewise, the docking barrier 81 may comprise a docking port 89 that removably couples with the charging port 41. The docking port 89 may be a counterposing male or female connector similar to the docking port 80 previously disclosed herein, or comprise a spring bias mechanism configured to facilitate coupling and decoupling. Alternatively, the charging port 41 may be a terminal, such as a metal contact, coupled about a periphery or circumference of the base connector 39, and the docking port 89 may be a complementary terminal disposed on one or more of the docking barriers 81.

In an exemplary embodiment, the base connector 39 is rotatably coupled to the movement module 32, and more particularly to the base coupler 37 of the base 33'. An actuator, such as a motor, may rotate the base connector 39 relative to the accessory post 30 (i.e., tubular member 35 comprising a portion of the accessory post 30, as illustrated in FIG. 3). The base connector 39 may rotate relative to the tubular member 35 to align the charging port 41 with the docking port 89 prior to docking of the autonomous accessory support 24 with the docking station 76'. Additionally or alternatively, the base connector 39 may be configured to rotate relative to the tubular member 35 within the cavity 85 after the autonomous accessory support 24 docks with the docking station 76'. For example, should the charging port 41 and the docking port 89 each comprise counterposing male and female connectors, the base connector 39 may rotate to align the charging port 41 as the autonomous accessory support 24 approaches the docking station 76'. In another example where the charging port 41 comprises a terminal disposed about a portion of the circumference of the base connector 39, the connector 39 may rotate within the cavity 85 of the docking station 76' to cause contact between the complementary terminals of the charging port 41 and the docking port 89.

In another exemplary embodiment, the charging port 41 comprises a terminal coupled about substantially an entirety of the circumference (e.g., 270 to 360 degrees) of the base connector 39. In such an embodiment, the terminal is configured to couple with the complementary terminal of the docking port 89 regardless of orientation of said autonomous accessory support relative to said docking station, both prior to and after docking.

The docking station 76' may comprise a movable gate (not shown). The movable gate may be pivotally coupled to the base section 77 and/or the docking barrier 81. In one example, a hinge and a biasing member couple the movable gate to the base section 77 between the barrier(s) and bias the movable gate so as to obstruct view of the cavity 85. For example, the movable gate is coupled via a hinge to the base section 77 and a torsion spring orients the movable gate in a generally vertical position at an end of the cavity 85. As the base 33' docks with the docking station 76', the base connector 39 contacts the movable gate with sufficient force to overcome the torsion spring. The moveable gate pivots to effectively flatten parallel to the base section 77, after which the base connector 39 can be moved within the cavity 85.

Once disposed within the cavity 85, the docking station 76' is configured to operably couple and supply power to the autonomous accessory support 24. Similar to the previously described embodiment of the docking station 76, the docking station 76 is in electrical communication with the power source 78, typically a common electrical outlet. Whereas the docking station 76 may comprise the docking port 80 to supply power, the docking station 76' of the present embodiment may supply power through electrical contacts and/or inductive charging. For example, the docking barrier 81, and more particularly the slotted portion 83b of the docking barrier 81, may comprise conductive contacts, such as metal strips, in electrical communication with the power source 78. The base connector 39, and more particularly the terminal portion 43b, may comprise conductive contacts in electrical communication with rechargeable power supply 38. When in direct contact, power is supplied from the power source 78 to the rechargeable power supply 38 via the contacts. Wireless charging such as inductive charging and otherwise may also be used through means commonly known in the art to electrically couple the power source 78 and the rechargeable power supply 38.

The autonomous accessory support 24 docks with the docking station 76, 76' for any number of reasons such as low battery, inactivity, user input, and the like. The docking station 76, 76' comprises a docking position module 88 in electronic communication with the controller 52 of the autonomous accessory support 24.

The docking module 88 provides a docking position signal to the controller 52. Based on the docking position signal, the controller 52 is configured to determine a second movement output signal and transmit the second movement output signal to the movement module 32. In response to the second movement output signal, the autonomous accessory support 24 autonomously moves to a docking position wherein the charging port 82 of the autonomous accessory support 24 engages the docking port 80.

In an exemplary embodiment, the tracking sensor 62 is in wireless communication with the docking position module 88. Data comprising the docking position is wirelessly transmitted from the docking position module 88 to the tracking sensor 62, then to the controller 52 of the autonomous accessory support 24. In another exemplary embodiment, data comprising the docking position is transmitted from the docking position module 88 to the LAN 86 via the data port 84, then from the LAN 86 to the autonomous accessory support 24 (wirelessly), then to the controller 52 of the autonomous accessory support 24. In yet another exemplary embodiment, the tracking sensor 62 is configured to detect the docking position module 88 through optical, infrared, acoustic or other means, particularly when the autonomous accessory support 24 and the docking station 76, 76' are reasonably proximate. Utilizing more than one of the above means for determining the second movement output signal is also contemplated. For example, should the autonomous accessory support 24 be operating on an opposite side of a medical floor of the medical facility 300 (FIG. 9), data comprising the docking position is wirelessly transmitted from the docking position module 88 to the controller 52 via the LAN 86. The controller 52 determines the second movement output signal based on the wirelessly received docking position signal. Once the autonomous accessory support 24 is suitably proximate and more precision is required for docking (e.g., coupling the docking port 80 and the charging port 82), the controller 52 may determine the second movement output signal based on the docking position signal detected by the tracking sensor 62 may use light-of-sight detection or infrared, acoustic or other means.

The second movement output signal, in a general sense, comprises a vector—a magnitude and a direction in which the autonomous accessory support 24 must move in order move to the docking position. In many respects, the second movement output signal is similar to the movement output signal associated with maintaining the autonomous accessory support 24 at the target patient proximity.

The autonomous accessory support 24 may dock with the docking station 76, 76' after a period of inactivity. The controller 52 is configured to determine the period of inactivity of the autonomous accessory support 24 based on an activity input signal. The period of inactivity may be based on any number of criteria selectable by the user. For example, the period of inactivity comprises a period of time during which power is not being supplied by the accessory port 36 to the medical accessory 26b. The treating medical professional may select, via the user input device 46, that the autonomous accessory support 24 return to and dock with the docking station 76, 76' after a period of time during which power is not being supplied to the pulse oximeter. After the patient 22 is decoupled from the medical line 28b of the medical accessory 26b (and/or the medical accessory 26b is powered off), the treating medical professional may continue to provide care without regard for ensuring the autonomous accessory support 24 is returned to the docking station 76, 76'.

Based on the activity input signal, controller 52 is configured to transmit the second movement output signal to the movement module 32 such that the autonomous accessory support 24 autonomously moves to the docking position and couples the charging port 82 and the docking port 80. As mentioned, the second movement output signal is determined by the controller 52 based on the docking position signal provided by the docking position module 88.

The user may manually instruct the autonomous accessory support 24 to dock with the docking station 76, 76'. More specifically, the treating medical professional may provide a user input signal to the controller 52 via the user input device 46. Based on the user input signal, the controller 52 is configured to transmit the second movement output signal to the movement module 32 such that the autonomous accessory support 24 autonomously moves to the docking position. The determination of the second movement output signal in response to the user input signal is described above.

Because the autonomous accessory support 24 generally moves with the patient 22, the movement of the autonomous accessory support 24 reflects the movement of the patient 22. In the context of patient assessment, treatment and rehabilitation, the autonomous accessory support system 20 advantageously acquires movement data that may be indicative of an early mobility state of the patient 22.

The autonomous accessory support 24 further comprises a memory device 90 in electronic communication with the controller 52, as illustrated in FIG. 4. The controller 52 is configured to store the movement data associated with the movement module 32 on the memory device 90. The movement data comprises at least one of distance, speed, and path traveled by the movement module 32 and reflective of the movement of the patient 22. Furthermore, the controller 52 may transmit the movement data to an electronic medical record (EMR) 92 (or electronic health record (EHR)) of the patient 22. In a general sense, the patient EMR 92 comprises a digital version of the medical and treatment history of the patient in a hospital or other medical facility.

Storing and/or transmitting the movement data to the patient EMR 92 facilitates improved patient care, particularly as medical facilities transition to an electronic environment. Valuable quantitative data is quickly accessible without tedious and resource-intensive data collection and recordation. For example, a patient 22 suffering from hypokalemia (i.e., low concentration of potassium in the blood) is coupled to an EKG to monitor heart rhythm and coupled to IV therapy of potassium supplementation. Each medical accessory is coupled to the patient via a medical line, resulting in a configuration similar to FIG. 1. As hypokalemia is often associated with fatigue and muscle weakness, treating medical providers may wish to determine the early mobility state of the patient which may be generally indicative of interval improvement of the hypokalemia. Typically, this requires a nurse or rehabilitation specialist monitoring the patient 22 during ambulation—each instance the patient 22 attempts to ambulate—and attempting to approximate how far the patient 22 has ambulated. In this example, the patient 22 walks two hundred feet at a speed of 1.6 miles per hour (mph), whereas average human walking speed is approximately 3.1 mph. Quantitatively ascertaining this data is difficult and resource-intensive. Knowing the patient 22 is ambulating at approximately fifty percent of baseline could be useful information in facilitating patient care, but the treating medical professionals often are unable to obtain such data without undue difficulty. Instead, the treating medical professionals often rely on subjective factors or otherwise decline to consider the early mobility state of the patient in facilitating the patient care. Further, and perhaps more useful than one instance of patient ambulation, having well-organized mobility data over the course of hours, days or weeks provides an accurate trajectory of patient improvement or deterioration.

For another example, once the treating medical professionals determine a patient 22 is capable of independent, unsupervised ambulation, an ambulation regimen may be implemented for the patient 22 to build strength and confidence. Because the autonomous accessory support 24 generally moves with the ambulating patient 22, the treating medical providers may ensure compliance with the ambulation regimen, as the movement data may be automatically stored and/or transmitted to the patient's EMR 92. This also fosters accountability of the patient 22, who knows the treating medical professionals are aware of any noncompliance with the ambulation regimen. Numerous other advantageous applications for tracking, storing, and/or transmitting movement data is contemplated by the present disclosure.

The movement data may be acquired by any number of means. A sensing device (e.g., Hall sensor) may be associated with the wheels 64 to determine the speed and/or distance traveled by the movement module 32. Alternatively or additionally, the path traveled by the movement module 32 may be determined by a global positioning system (GPS) or the locator network 302 associated with the medical facility 300, or any other wireless tracking means commonly known in the art.

Not limited to movement data, the memory device 90 of the autonomous accessory support 24 may store physiologic and other types of data. The medical accessories 26*a*, 26*b* may be in electronic communication with the controller 52 via the data port 44 on the accessory post 30. For example, the pulse oximeter console of FIG. 1 may continuously monitor the pulse oximetry of the patient 22, and the resulting data may stored in the memory device 90. In another example, the quantity of IV therapy administered to the patient 22, as measured by an accessory sensor 50, may be stored in the memory device 90. These metrics may be transmitted to the patient EMR 92 for convenient review by treating medical professionals. Together with the movement data, the patient EMR 92 is populated with robust data regarding the patient 22 to facilitate improved patient care.

Another example of functionality outside of movement tracking and data comprises detecting characteristics of the environment surrounding the patient. The autonomous accessory support 24 may comprise sensors (not shown) configured to any number and type of environmental characteristics. For example, the sensor(s) may detect smoke or heat in the case of fire. In response, the indicator device 54 alerts the patient 22 and/or the caregiver stationed within the medical facility 300 via the LAN 84. In another example, the sensor(s) detect cigarette smoke and provide an audible or visual alert with the indicator device 54. The caregiver may be alerted and the incident may be logged in the patient EMR 92 as previously described herein. A further example may comprise the sensor(s) detecting the ambient light, or lack thereof, and powering up or down the various electronic components of the autonomous accessory support 24. Other related functionality is similarly contemplated.

The transmission of the movement data and/or other data to the patient EMR 92 occurs wirelessly via the wireless antenna 40 in electronic communication with the controller 52, or upon docking of the autonomous accessory support 24 and the docking station 76, 76' in the manner previously disclosed herein. The controller 52 transmits the movement data and/or other data to the LAN 86 associated with the medical facility 300. The patient EMR 92 is generally comprised of software accessible by and integrated with the LAN 86. In other words, the movement data and/or other data is uploaded from memory device 90 to the patient EMR 92 via the LAN 86.

The medical facility 300 may comprise one or more dashboard systems (not shown) providing a user interface and display for the autonomous accessory support systems 20, 20', 20". The dashboard may comprise a display and input device positioned at any reasonable location within the medical facility. Additionally or alternatively, the dashboard is integrated into software operating on existing hospital hardware architecture.

The dashboard receives via the LAN 82 of the medical facility 300 information related to one or more of the autonomous accessory supports 24. The dashboard displays operating conditions for each of the autonomous accessory supports 24, including a number of units deployed about the medical facility 300, a number of units docked with docking stations, battery life of each of the autonomous accessory supports 24, and the like. The dashboard may receive information, alerts, and/or alarms from the autonomous accessory supports 24 for any type of event described herein. The dashboard may summon one or more of the autonomous accessory supports 24 to a particular location within the medical facility 300. Other related features of such a dashboard are readily apparent to those having skill in the art.

Figure 7:
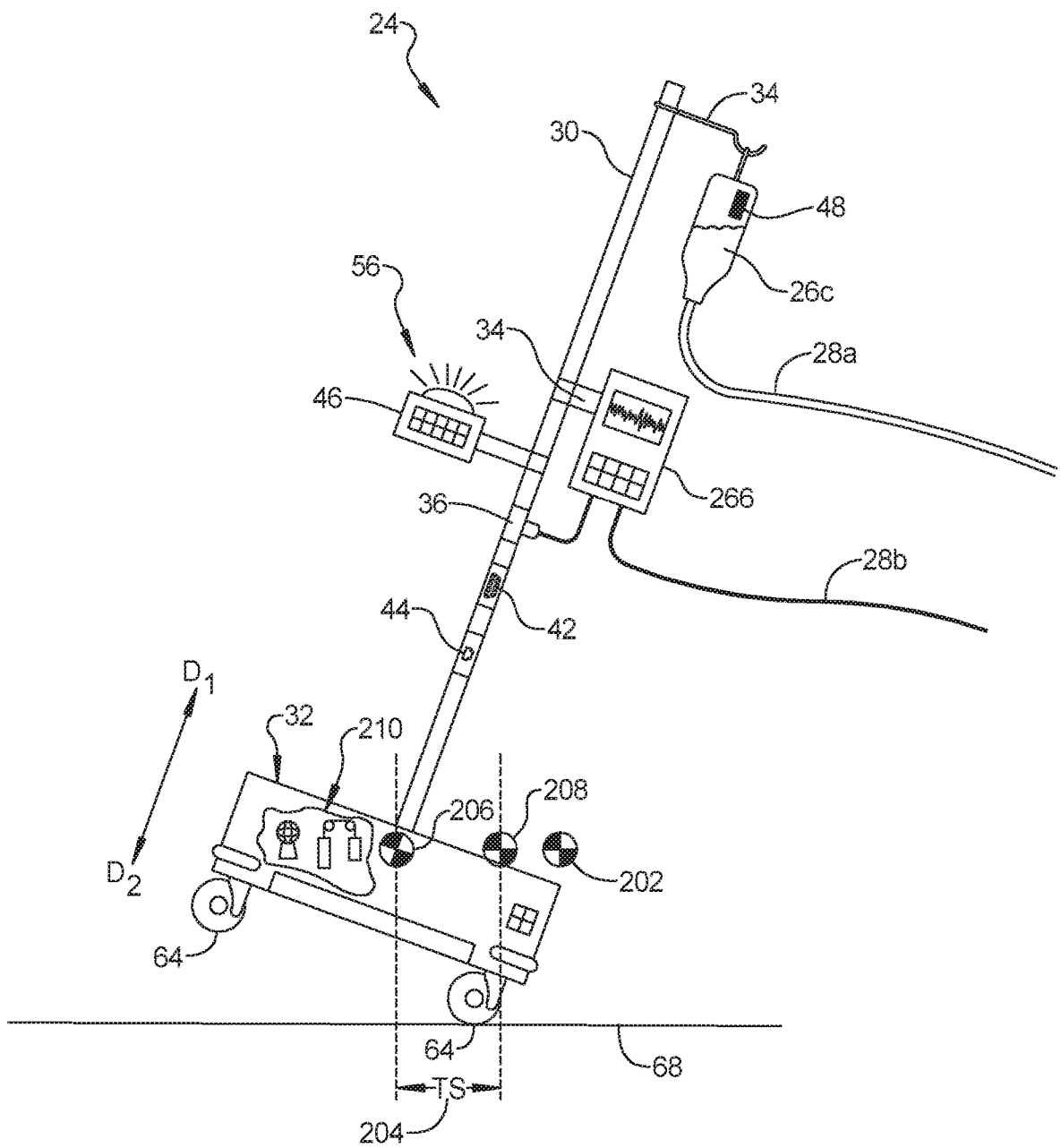
FIG. 7 is an elevational view of the autonomous accessory support of FIG. 1 in a position of instability in accordance to the embodiments of the present disclosure, with a schematic diagram of an instability module in accordance with an exemplary embodiment of the present disclosure.

Those having skill in the art readily appreciate that the accessory post 30 supporting medical accessories 26*a*-26*e* at an appreciable height above the floor surface 68 is associated with the risk of instability. The risk is enhanced by the potential for sudden forces perpendicular to the accessory post 30 via the medical lines 28*a*-28*e* coupled to the patient 22, as well as environmental obstacles (e.g., ramps, obstructions, etc.). FIG. 7 illustrates an exemplary scenario where the autonomous accessory support 24 is experiencing instability. To ensure the autonomous accessory support 24 remains safely upright, the autonomous accessory support system 20, 20', 20" may further comprise a stability module 200.

With reference to FIG. 4 and continued reference to FIG. 7, the stability module 200 is in electronic communication with the controller 52. The stability module 200 is configured to determine an instability factor of the autonomous accessory support 24. In one example, the instability factor is defined as an instantaneous center of gravity 202 of the autonomous accessory support 24 exceeding a threshold of safety 204. More specifically, the autonomous accessory support 24 is designed to comprise a "true" center of gravity 206 that is substantially centered on the movement module 32 when the medical accessory 26a-26e is coupled to the accessory post 30 and the movement module 32 is at rest. Typically, the accessory post 30 is positioned at a center of the base 33 of the movement module 32 for improved stability in all directions.

With most physical objects, a threshold center of gravity 208 exists such that should an instantaneous center of gravity 202 be at a greater distance from the true center of gravity 206 than the threshold center of gravity 208, the autonomous accessory support 24 topples. In FIG. 7, the difference between the center of gravity 206 and the threshold center of gravity 208 may define the threshold of safety 204. The threshold of safety 204 changes based on the weight of the medical accessory 26a-26e, the speed at which the autonomous accessory support 24 is moving, and the like. The stability module 200 is configured to determine the threshold of safety 204 in a continuous manner.

Likewise, the stability module 200 is configured to determine the instability factor in a continuous manner. For example, the instability factor may be a percentage of the threshold of safety 204 "consumed" based on the instantaneous center of gravity 202. In other words, the instability factor may be a ratio of the instantaneous center of gravity 202 to the threshold center of gravity 208. In a general sense, the instability factor is a quantitative determination of the likelihood that the autonomous accessory support 24 will topple.

Should the instability factor, as determined by the stability module 200, exceed a predetermined threshold, the controller 52 may activate the indicator device 54. The predetermined threshold may or may not be the threshold of safety 204. Preferably, the predetermined threshold is a factor of safety less than the threshold of safety 204 so as to permit the user to take remedial action. In one example, the predetermined threshold is 80% of the threshold of safety 204. The indicator device 54 provides an audible and/or visual alert through an indicator to the user should the instability factor 200 exceed the predetermined threshold.

Furthermore, should the instability factor, as determined by the stability module 200, exceed the predetermined threshold, the controller 52 may provide a corrective response. In one example, the stability module 200 is configured to adjust the instantaneous center of gravity 202 of the autonomous accessory support 24 to reduce the instability factor. To do so, the stability module 200 may further comprise a weight distribution mechanism 210 comprising movable mass(es), gyroscopes, and the like. Using the illustrative embodiment of FIG. 7 with the autonomous accessory support 24 at risk of toppling in the direction D1, the weight distribution mechanism 210 causes the instantaneous center of gravity 202 to move towards the true center of gravity 206, at least within the threshold of safety 204, such that the autonomous accessory support 24 moves in the direction D2 until the wheels 64 return to contact with the floor surface 68.

To ensure safe and efficient movement, the autonomous accessory support 24 may be equipped with several additional features, including movement sensors 70 and touch-sensitive bumpers 72. The movement sensors 70 detect obstructions such as objects and/or obstacles such as gaps, steps, ramps, and the like. More specifically, the movement sensors 70 are coupled to the movement module 32 in such a manner to detect obstructions and/or obstacles at or near ground level. The movement sensors 70 may be infrared (IR) sensors, acoustic sensors (e.g., SONAR), or any suitable means to detect obstructions and obstacles at a distance. If the movement sensors 70 detect an obstruction or obstacle, the controller 52 is configured to react accordingly. Most often, the controller 52 determines an alternative path to circumvent the obstruction or obstacle. In instances of significant obstruction or obstacle, such as stairs, the controller 52 may instruct the movement module 32 to stop, after which an alert is provided to the user via the indicator device 54 or otherwise. In response to the alert(s), the user may be required to manually assist the autonomous accessory support 24 to traverse the more demanding obstruction or obstacle.

The touch-sensitive bumpers 72 may be coupled about an exterior of the movement module 32. In the illustrated embodiment of FIGS. 1 and 2, the touch-sensitive bumpers 72 are coupled about each of the four vertical edges of the base 33 of the movement module 32. The touch-sensitive bumpers 72 are comprised of an elastic material to resiliently absorb energy should the autonomous accessory support 24 collide with an object such as a wall. Furthermore, the touch-sensitive bumpers 72 comprise an internal sensor in electronic communication with the controller 52. The internal sensor is configured to provide an electronic signal to the controller 52 in response to the touch-sensitive bumpers 72 elastically deforming beyond a predetermined threshold. Based on the electronic signal, and often in conjunction with the movement sensors 70, the controller 52 determines an alternative path and/or provides an alert to the user via the indicator device 54.

In addition to reducing or maintaining a target patient proximity or preset distance, the autonomous accessory support 24 may further comprise an orientation module 63 (FIGS. 2 and 4). The orientation module 63 is configured to prevent the medical line 28a-28e from wrapping around the accessory post 30. The orientation module 63 is in electronic communication with the controller 52 to determine a reference orientation and determine and monitor angular displacement. The determination of the reference orientation may be in response to a user input to the user input device 46, or automatically as a startup sequence during operation. The angular displacement may be defined as an amount of rotation about an axis defined by the accessory post 30. The orientation module 63 may comprise gyroscopes, accelerometers, or other sensors to monitor the angular displacement. In another example, the orientation module 63 monitors the relative movement of the wheels 64 coupled to the movement module to determine the angular displacement. The angular displacement may also be used to determine the directional component of the position of the patient 22 being tracked by the tracking module 58.

Should the angular displacement in a particular direction exceed a requisite threshold, the orientation module 63 transmits a signal to the controller 52. For example, during operation the movement module 32 rotates clockwise by 270°, which at least partially wraps the medical line 28a-28e about the accessory post 30. The orientation module 63 transmits a signal to the controller 52 to rotate the movement module 32 (or the accessory post 30) counterclockwise by 270°, after which the instantaneous orientation equals the reference orientation. In another example, the orientation module 63 maintains the instantaneous orientation within a predetermined range of the reference orientation such as 5°, 10°, or 20°. Furthermore, the orientation module 63 may adjust the reference orientation accordingly as the movement module 32 performs turning maneuvers during normal operation (i.e., concurrent translational movement of the movement module 32).

In at least some embodiments, the autonomous accessory support further comprises a disinfection module 74. The disinfection module is configured to disinfect floor surface underneath the autonomous accessory support as the autonomous accessory support moves along the floor. In one embodiment, the disinfection module comprises an ultraviolet (UV) light device 74 configured to disinfect the floor surface as the autonomous accessory support moves along the floor during movement of the autonomous accessory support 24. The UV device 74 may be coupled to the underside 66 of the base 33 of the movement module 32. The UV device 74 comprises one or more bulbs configured to emanate or output light within the ultraviolet spectrum. The UV device utilizes short-wavelength ultraviolet (UV-C) light to kill or inactivate microorganisms by destroying nucleic acids and disrupting their DNA. The UV device 74 may coupled to the rechargeable power supply 38 and in electronic communication with the controller 52.

The autonomous accessory support 24 may comprise additional functionality to improve the delivery of therapy to a patient 22. For example, the autonomous accessory support assists with ensuring accuracy with the type and/or dosage of IV therapy administered. The medical accessory 26a may comprise indicia 48 unique to a specific type of IV therapy. For example, a barcode or passive RFID identification tag is disposed on the IV bag, as illustrated in FIG. 1. Once the IV bag is coupled to the accessory post 30, typically by suspending the IV bag from the coupling mechanism 34, the accessory sensor 50 such as an optical sensor or an electromagnetic sensor reads or detects the barcode or the RFID signal, respectively. A comparison is made between the indicia 48 read or detected by the accessory sensor 50 and a specific type of IV therapy to be administered. The type of IV therapy to be administered is input by the user via the user input device 46 to determine from the patient EMR 92 or electronic patient chart. The time of administration of the IV therapy may similarly be verified with the patient EMR 92 or the electronic patient chart accessible by the controller 52. Alternatively or additionally, the comparison may be performed remotely from the autonomous accessory support 24. In such an example, an electronic signal associated with each of the indicia 48 read or detected by the accessory sensor 50 and the specific type of IV therapy to be administered is transmitted to a remote computer to perform the comparison.

If the indicia 48 read or detected by the accessory sensor 50 does not match the specific type of IV therapy to be administered, the user may be alerted. The indicator device 54 is in electronic communication with the controller 52 and configured to provide an alert. The alert is typically audible, visual, tactile or a combination thereof. FIG. 1 shows the indicator device 54 comprising a speaker disposed atop the user input device 46. Alternatively or additionally, the indicator device 54 comprises a light source associated with the accessory post 30, or a portion thereof, that illuminates to alert the user. The present disclosure contemplates that the alert may be sent via the wireless antenna 40 to a nurses' station, physician's smartphone, or any other desired receiving device.

If the indicia 48 read or detected by the accessory sensor 50 does not match the specific type of IV therapy to be administered, additional action may include terminating the delivery of the IV therapy. In one example, a pump is turned off and/or a valve actuated to prevent the IV therapy from reaching the patient 22. Furthermore, a quantity of therapy remaining in the IV bag may be detected through means commonly known in the art including, but not limited to, load sensing, optical sensing, and the like. Should the quantity of IV therapy in the IV bag become undesirably low, an alert may be provided to the user and/or a treating medical provider through the indicator device 54 or means commonly known in the art.

Figure 8A:
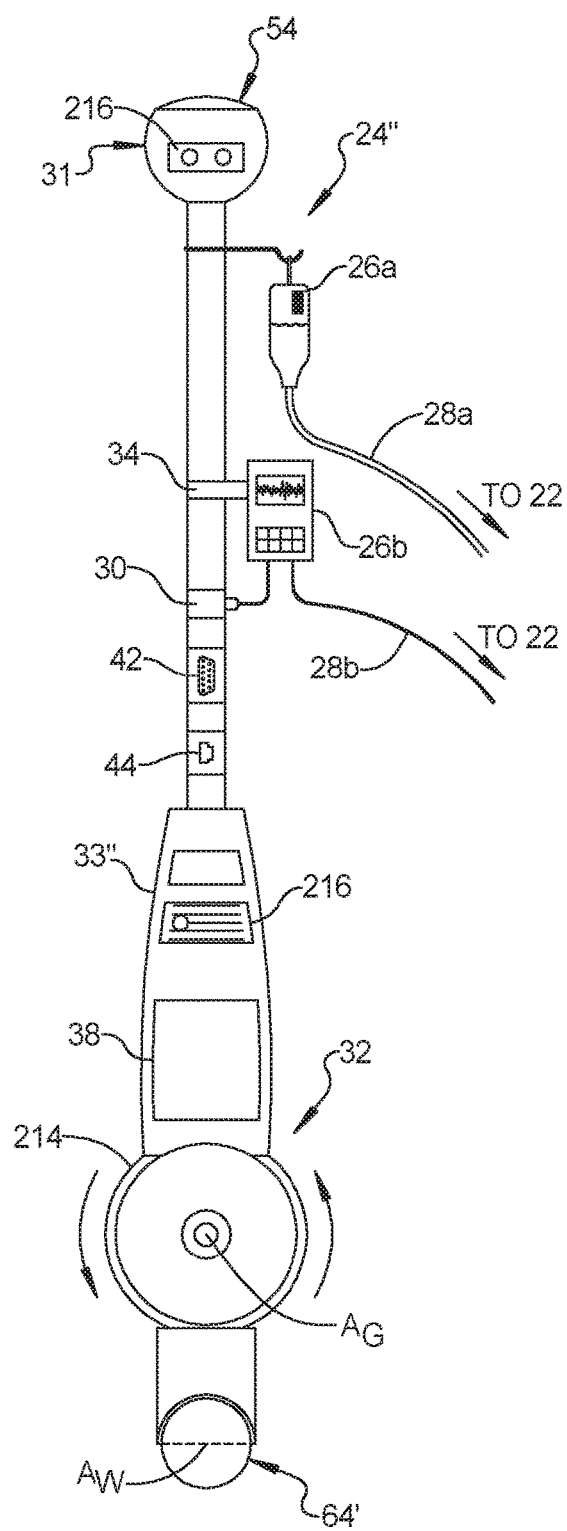
FIG. 8A is an elevational view of an autonomous accessory support in accordance with another exemplary embodiment of the present disclosure.
Figure 8B:
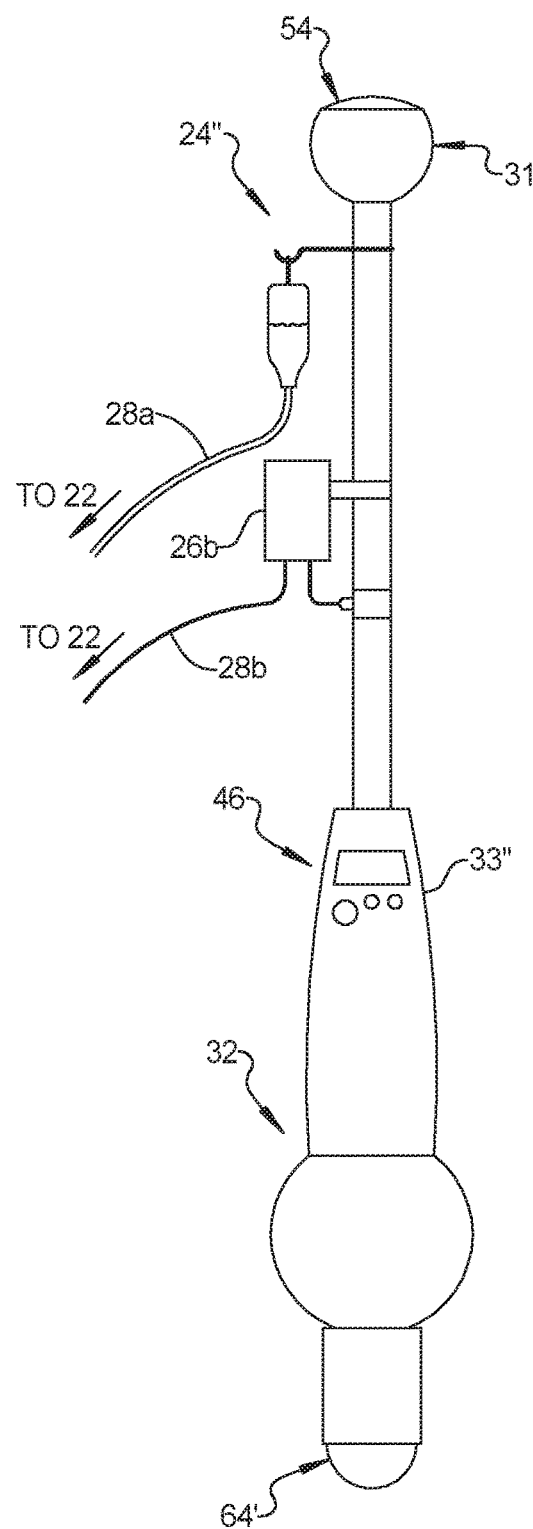
FIG. 8B is an elevational view of the autonomous accessory support of FIG. 8A.

Referring to FIGS. 8A and 8B, an autonomous accessory support 24" in accordance with another exemplary embodiment of the present disclosure is illustrated. The autonomous accessory support 24" comprises the accessory post 30 and the movement module 32. The accessory post 30 is oriented vertically and extending upwardly from the movement module 32 such that the movement module 32 supports the accessory post 30. The accessory post 30 comprises coupling mechanisms 34 that couple the medical accessories 26a, 26b to the accessory post 30. The autonomous accessory support 24" comprises any number of additional components previously described herein, including but not limited to the power port 36, the rechargeable power supply 38, the wireless antenna, the 37-pin connector 42, the data port 44, the user input device 46, the tracking module 58, the accessory sensor 50, the indicator device 54, additional sensors (e.g., infrared, ultraviolet, touch, proximity, temperature, etc.), the call button, the fluid port, and other input and output ports. FIGS. 8A and 8B illustrate an exemplary user input device 46 comprising an output screen and input means disposed on a base 33" of the movement module 32'. The indicator device 54 of the present embodiment comprises a status light positioned proximate to the top of the accessory post 30. More specifically, the accessory post 30 comprises a head unit 31 coupled to the accessory post 30 opposite the base 33". The illustrated head unit 31 is substantially spherical, but any suitable shape is contemplated. The indicator device 54 comprising the status light is positioned on an uppermost portion of the head unit 31.

Whereas previously described embodiments of the movement module 32 comprise the base 33 and wheels 64, the base 33" of the movement module 32 of the present embodiment comprises a singular powered wheel 64'. As illustrated in FIGS. 8A and 8B, the singular powered wheel 64' is positioned substantially inline with the accessory post 30 and a movement module 32'. Further, the base 33" of the movement module 32' may be elongated such that substantially an entirely of the autonomous accessory support 24" is elongated and rod-like in appearance. The singular powered wheel 64' provides a singular point or area of contact with the floor surface 48 for the autonomous accessory support 24". In other words, the singular powered wheel 64' wholly supports the base 33" and the accessory post 30. Among other advantages, the exemplary embodiment illustrated in FIGS. 8A and 8B minimize the footprint of the autonomous accessory support 24", particularly when moving autonomously when coupled to the patient 24 with a medical line 28a, 28b.

Consistent with the previously described embodiments, the singular powered wheel 64' moves the movement module 32 of the autonomous accessory support 24" in response to a movement output signal from the controller 52 (see FIG. 4). Those having skill in the art readily appreciate that the elongated design of the autonomous accessory support 24"

of FIGS. 8A and 8B subjects the autonomous accessory support 24" to instability during movement.

The autonomous accessory support 24" may comprise the previously described stability module 200 configured to maintain appropriate balance of the autonomous accessory support 24". In at least one embodiment, the stability module 200 is configured to determine an instability factor of the autonomous accessory support 24" defined as an instantaneous center of gravity 202 exceeding a threshold of safety 204 (see FIG. 7). Should the instability factor, as determined by the stability module 200, exceed a predetermined threshold, the controller 52 may be configured to provide a corrective response.

Referring to FIGS. 8A and 8B, the stability module 200 of the autonomous accessory support 24" of the present embodiment may comprise one or more gyroscopes 214. The gyroscope 214 may comprise one or more wheels having relatively high mass configured to rotate at a high spin rate to stabilize the autonomous accessory support 24". In operation, the gyroscope 214 is configured to counteract forces parallel to the gyroscope axis orthogonal to the rotating mass (e.g., forces that would cause the autonomous accessory support 24" to tip). In the exemplary embodiment illustrated in FIGS. 8A and 8B, the gyroscope 214 is coupled to the base 33" of the movement module 32' proximate to the singular powered wheel 64'. Positioning the gyroscope 214 relatively closer to the floor surface 48 may provide improved stabilization with wheels of lesser mass and/or at lesser spin rates, but the present disclosure contemplates the gyroscope 214 may be coupled to the base 33", the accessory post 30, or any suitable structure on the autonomous accessory support 24". Further, an axis $A_G$ about which the gyroscope 214 rotates may be orthogonal to an axis $A_W$ about which the singular powered wheel 64' rotates.

As commonly known in the art, the greater the rotating mass and/or the higher spin rate provides greater angular velocity sufficient to counteract stronger forces orthogonal to the rotating mass. Thus, the gyroscope 214 rotates to maintain orientation of the output axis defined longitudinally along the elongated autonomous accessory support 24". Any suitable mass of the gyroscope 214 is contemplated and the spin rate selectively controlled by a motor (not shown) in electronic communication with the controller 56 and/or the stability module 200. The spin rate may be determined by the stability module 200 comprising one or more accelerometers 216 and/or other sensors. The accelerometer 216 may be coupled to any suitable structure of the autonomous accessory support 24". For example, in the exemplary embodiment illustrated in FIGS. 8A and 8B, accelerometers 216 are coupled to the head unit 31 and the base unit 33". The accelerometers 216 of the stability module 200 may be in electronic communication with the controller 54.

In many respects the operation of the autonomous accessory support 24" of the present embodiment is the same as those previously discussed. The tracking module 58 tracks movement of the patient 22 or a patient support apparatus 100 relative to the autonomous accessory support 20 and provide a tracking input signal. The controller 54 is in electronic communication with said tracking module 58. The controller 54 determines a target patient proximity being a distance between the autonomous accessory support 24" and the patient 22 or the patient support apparatus 100 sufficient to prevent tensioning of the medical line 28a, 28b beyond a tension threshold. The controller 54 further determines an actual patient proximity based on the tracking input signal, and a movement output signal based on the target patient proximity and the actual patient proximity. The controller 54 transmits the movement output signal to the movement module 32.

The singular powered wheel 64 is controllable by the movement module 32. Either prior to or during movement of the movement module 32, the autonomous accessory support 24" may be subject to instability. The stability module 200 comprising the gyroscope 214 is configured to determine an instability factor of the autonomous accessory support 24" and provide an instability signal. In response to the instability signal, the controller 54 may transmit a stability output signal to the movement module 32 to operate said singular powered wheel 64' to stabilize the autonomous accessory support 24". Effectively, operation of the singular powered wheel 64' offsets the momentum of the autonomous accessory support 24" against the direction of instability. In another exemplary embodiment, the singular powered wheel 64' comprises two wheels, and the base 33" comprises one or more servomotors. In such an embodiment, the two wheels have a relatively small footprint and the wheels are configured to offset any instability based on automated attitude adjustment of the gyroscope 214.

The controller 54 may transmit a second stability output signal to said stability module 200 to operate the gyroscope 214 to further stabilize the autonomous accessory support 24". Operation of the gyroscope 214 comprises increasing or decreasing the spin rate, and/or increasing or decreasing an adjustable mass. Consequently, the autonomous accessory support 24" remains substantially upright, as illustrated in FIGS. 8A and 8B, as it autonomously tracks the movement of the patient 22 or patient support apparatus 100. The present disclosure contemplates that the features of the autonomous accessory support system 20, 20', 20" described throughout the present disclosure are considered incorporated by reference in the present embodiment of the autonomous accessory support 24".

Referring again to FIG. 9, an exemplary scenario in which the autonomous accessory support system 20, 20', 20" will be described. A medical facility 300 may comprise a floor from a hospital, including an operating theatre 304, patient rooms 306a-d, and a clinic 308. Two corridors 310a, 310b access each of the areas and are connected by a ramp 312. The medical facility 300 further includes an elevator 313 to move between different floors. FIG. 9 shows the patient support apparatus 100 being tracked by the autonomous accessory support 24.

In an illustrative example shown in FIG. 9, the patient 22 supported on the patient support apparatus 100 and coupled to the autonomous accessory support 24 via the medical line 28, leaves the operating theatre 304 with the patient room 306d being the destination. The locator network 302, via the sensors 314 or otherwise, is continuously tracking the tracking module 58 of the autonomous accessory support 24 and the tracking device 60b of the patient support apparatus 100. Further, the locator network 302 generates a first location input signal and a second location input signal based on the locations of the tracking device 60b and the tracking module 58, respectively. The tracking module 58 provides the tracking input signal (to the controller 52) based on the first location input signal and the second location input signal. The controller 52 determines the actual patient proximity based on the tracking input signal.

As the patient support apparatus 100 moves through the corridor 310a relative to the autonomous accessory support 24, at some instant the actual patient proximity is greater than the target patient proximity (or the preset distance). The controller 52 determines the movement output signal, and transmits the same to the movement module 32 of the autonomous accessory support 24 to reduce the actual patient proximity to the target patient proximity (or to maintain the preset distance). As mentioned, the movement output signal, in a general sense, comprises a directional component such that the autonomous accessory support 24 follows the path of the patient 22 (or some offset thereof). The magnitude component of the movement output signal may be the speed of the patient 22 relative to the autonomous accessory support 24 in order to match the speed of the autonomous accessory support 24 to that of the patient 22.

The autonomous accessory support 24 follows the patient support apparatus 100 down the ramp 312. Yet, as the autonomous accessory support 24 descends the ramp 312, its instantaneous center of gravity 202 changes. With concurrent reference to FIG. 7, the stability module 200, which is continuously determining the instantaneous center of gravity 202 and the threshold of safety 204, operates in the manner previously disclosed herein. In short, the stability module 200 determines the instability factor of the autonomous accessory support 24, and should the instability factor exceed the predetermined threshold, an alert is provided via the indicator device 54. The stability module 200 may also provide the corrective response such as adjusting the instantaneous center of gravity 202 with the weight distribution system 210 such that the autonomous accessory support 24 safely descends the ramp 312.

The autonomous accessory support 24 continues its operation in the second corridor 310b. The movement sensors 70 detect an obstruction 316 within the corridor 310b. The movement sensors 70 provide an obstruction signal to the controller 52. In response to the obstruction signal, the controller 52 may determine an alternative path to circumvent the obstruction 316. In the illustrative example of FIG. 9, the alternative path comprises moving laterally until the obstruction 316 is no longer detected by the movement sensors 70. In so doing, the controller 52 determines the movement output signal that compensates for the increase in actual patient proximity that occurs while the movement module 32 is moving laterally (and the patient support apparatus 100 is moving longitudinally through the corridor 310b). In such an example, the magnitude component of the movement output signal is increased (i.e., the movement module 32 speeds up) to ensure the autonomous accessory support 24 remains less than or equal to the target patient proximity (or preset distance) to the patient support apparatus 100.

Similarly, as the patient support apparatus 100 enters the patient room 306d, the movement sensors 70 detect the doorway. Should insufficient time be available to avoid a collision, the touch-sensitive bumpers 72 elastically compress to avoid damage to the autonomous accessory support 24 and the doorway. During the elastic compression, sensors of the touch-sensitive bumpers 72 send a collision signal to the controller 52. In response to the collision signal, the controller 52 may determine the suitable course of action, most often determining an alternative path. If no such path is apparent, as determined by the controller 52, an alert may be provided via the indicator device 54.

Once in the patient room 306d, the treating medical professional may decide to decouple the autonomous accessory support 24 from the patient 22. In one example, the treating medical professional may elect to autonomously send the autonomous accessory support 24 to the docking station 76, 76'. The treating medical professional provides a user input to the user input device 46, which provides the user input signal to the controller 52. The locator network 302 is in electronic communication with the docking position module 88 of the docking station 76, 76'. The sensors 314 of the locator network 312 may be configured to detect the docking position of the docking station 76, 76' based on wireless detection of the docking position module 88. The locator network 302 generates the docking position signal indicative of the docking position. The locator network 302, via the sensors 312 or otherwise, also generate the second location input signal based on the location of the tracking module 58 of the autonomous accessory support 24. Each of the docking position signal and the second location input signal are received by the controller 52 from the locator network 302. The controller 52 determines the second movement output signal based on the docking position signal and/or the second location input signal. The second movement output signal is transmitted to the movement module 32 to move the autonomous accessory support 24 to the docking position. During the movement to the docking position, the autonomous accessory support 24 avoids obstacles and maintains stability as disclosed herein.

Upon arriving at the docking position, the charging port 82 of the autonomous accessory support 24 engages the docking port 80 of the docking station 76, 76'. The docking station 76, 76', in electrical coupling with the power source 76, recharges the rechargeable power supply 38 of the autonomous accessory support 24. Transferring of movement data, physiologic data, or other data stored on the memory device 90 to the patient EMR 92 via the LAN 86 of the medical facility 300 may also be accomplished. The data may also be transferred wirelessly via the wireless antenna 40 to wireless receivers associated with the LAN 86 of the medical facility 300. Furthermore, during all movements of the autonomous accessory support 24, the UV device 74 may be disinfecting the floor. A disinfecting report detailing the area disinfected (in square feet) or time the UV device 74 was activated may be stored on the memory device 90 and/or transferred to a device via the LAN 86 of the medical facility 300.

In one example, the autonomous accessory support 24 is initially docked at the docking station 76, 76' on the floor of the medical facility 300 of FIG. 9. A medical professional on another floor (not shown), and having a user device remote from the autonomous accessory support 24 (e.g., a smartphone), may summon the autonomous accessory support 24. The autonomous accessory support 24 may be configured to decouple from the docking station 76, 76', navigate the corridors 310a, 310b, and electronically operate the elevator 313 to travel to the appropriate floor. One exemplary method of doing so is disclosed in U.S. Pat. Pub. No. 2007/0129849, filed on Oct. 16, 2006, which is incorporated by reference in its entirety.

In another exemplary embodiment, the autonomous accessory support 24 may be configured to store a floorplan of the medical facility 300. More particularly, the floorplan may be stored in the memory device 90. The stored floorplan may identify obstructions such as walls, capital equipment, stairs, ramps, elevators, etc. Whereas the above described embodiment primarily relied on real-time detection of the obstructions, the autonomous accessory support 24 may additionally use the stored floorplan to improve travel within the medical facility 300. In one example, the autonomous accessory support 24 relies solely on the stored floorplan.

The floorplan may be uploaded or otherwise transmitted to the memory device 90 of the autonomous accessory support 24, or alternatively be constructed by the autonomous accessory support 24 itself as it moves about the medical facility 300. In the latter instance, the movement sensors 70, the touch-sensitive bumpers 72, and other sensors may collect data. The rendering of floorplan useable by the autonomous accessory support 24 may be performed by the controller 52, and/or remotely by other software. In some examples, the stored floorplan is partially rendered by the autonomous accessory support 24 and manually supplemented by an individual utilizing software designed for the same.

The stored floorplan may be updated each instance the autonomous accessory support 24 moves about the medical facility 300. Sensors 314 of the locator network 302 of the medical facility 300 may provide landmarks by which the autonomous accessory support 24 determines if modifications to the medical facility 300 have occurred (e.g., rearrangement of medical equipment). Additionally or alternatively, the sensors 314 of the locator network 302 may transmit the position of the autonomous accessory support 24 to the controller 52 for determination of interval rearrangements.

Based on the stored floorplan, the autonomous accessory support 24 may be configured to make route determinations. For example, should the autonomous accessory support 24 require descending the ramp 312 of the medical facility 300, the controller 52 may determine an alternate route based on the stored floorplan. Other related operations are contemplated using the stored floorplan of the medical facility 300.

Figure 10:
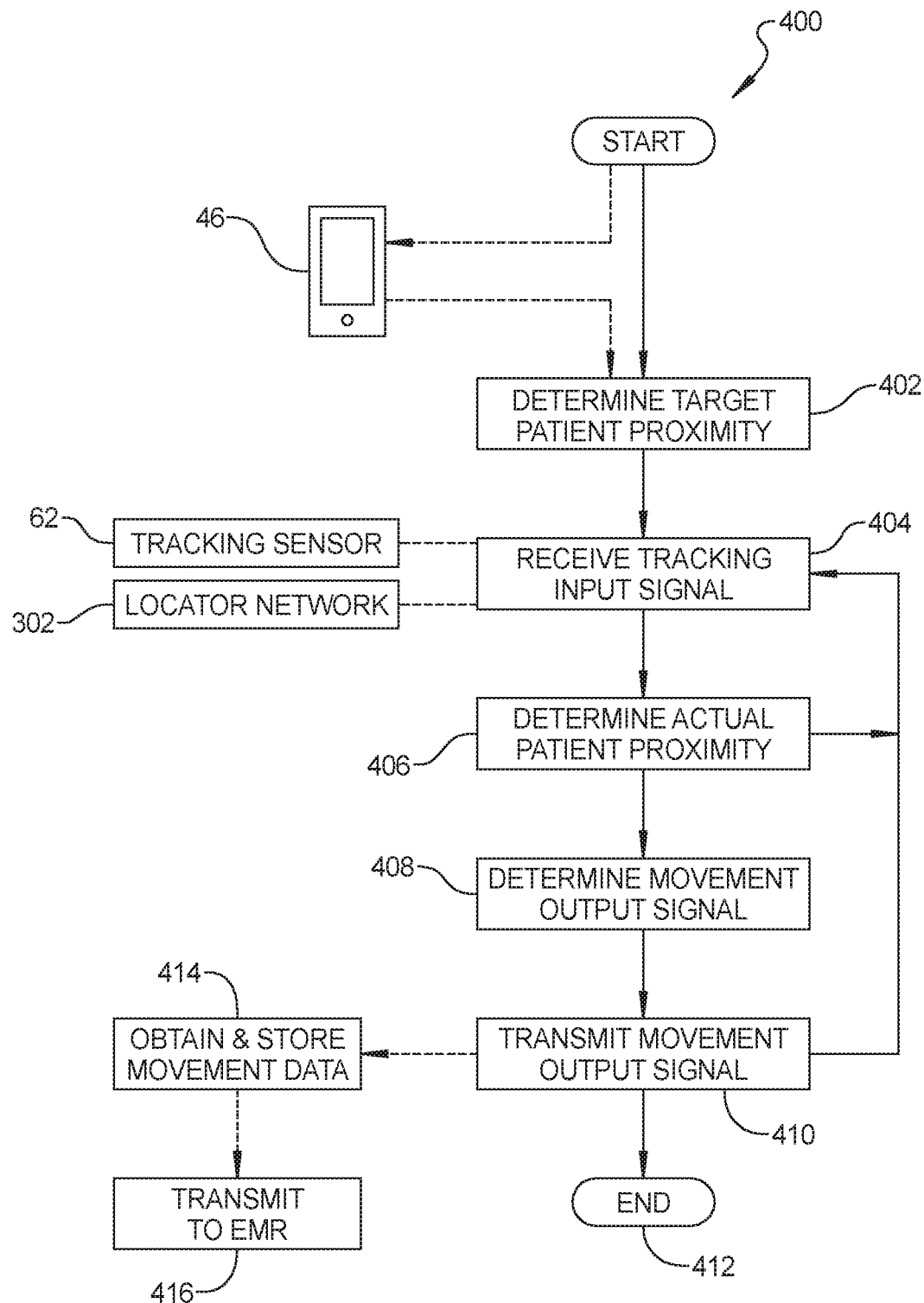
FIG. 10 is a schematic diagram detailing exemplary operation of the autonomous accessory support system in accordance with certain embodiments of the present disclosure.

Methods for operating the autonomous accessory support 24 and/or system 20, 20', 20" are also contemplated. Referring to FIG. 10, an exemplary method 400 is illustrated. The method 400 comprises determining the target patient proximity (step 402). The target patient proximity is the distance between the autonomous accessory support 24 and the patient 22 or the patient support apparatus 100 sufficient to prevent tensioning of the medical line 28a-28e beyond the tension threshold. The target patient proximity may be entered via the user input device 46 or based on an initial suitable position of the patient 22 relative to the medical accessory 26a-26e. In one example, the length of the medical line 28a-28e is entered into the user input device 46 or the type of medical line 28a-28e is selected from a database containing corresponding known lengths. After the target patient proximity is determined, the controller 52 receives the tracking input signal provided by the tracking module 58 (step 404). The tracking input signal is based on the movement of the patient 22 tracked by the tracking module 58. As illustrated in FIG. 10, the tracking input signal may be generated in part by the tracking sensor 62 on the autonomous accessory support 24 detecting the tracking device 60a, 60b on the patient 22 and/or the patient support apparatus 100. Alternatively or additionally, the tracking input signal may be generated in part by the locator network 302 of the medical facility 300 as previously described herein.

After the controller 52 receives the tracking input signal, the controller 52 determines the actual patient proximity (step 406). The actual patient proximity is based on the tracking input signal. The actual patient proximity may be a distance, a vector, coordinates, and the like. Thereafter, the controller 52 determines the movement output signal based on the target patient proximity and the actual patient proximity (step 408). In one example, the controller 52 first determines if the actual patient proximity is greater than the target patient proximity. If negative, the controller 52 does not generate a movement output signal and the method 400 returns to step 404. If affirmative, the controller 52 may perform numerical calculations to most efficiently reduce the actual patient proximity to the target patient proximity. Often, the resulting movement output signal has a directional component directly towards the autonomous accessory support 24 (i.e., a straight line) and a magnitude component of a speed greater than the recently determined speed of the patient 22 or the patient support apparatus 100. As disclosed herein, other considerations may influence the determined movement output signal such as obstacles or obstructions, changes in center of gravity, and the like.

After the movement output signal is generated, the method 400 further comprises the step of transmitting the movement output signal to the movement module 32 (step 410). In response to the transmitted movement output signal, the movement module 32 moves accordingly to reduce the actual patient proximity to the target patient proximity. Thereafter, the method 400 returns to step 404, after which steps 404 through 410 loop to maintain the actual patient proximity at the target patient proximity. Those having skill in the art appreciate that particular feedback controls may be incorporated to prevent "jerkiness" at the target patient proximity (e.g., filtering and smoothing algorithms).

Once the autonomous accessory support 24 is no longer tracking the movement of the patient 22 or the patient support apparatus 100, the method 400 ends (step 412). Either prior to or after step 412, the movement data may be obtained and stored on the memory device 90 (step 414). The movement data may be transmitted to the patient EMR (step 416).

Figure 11:
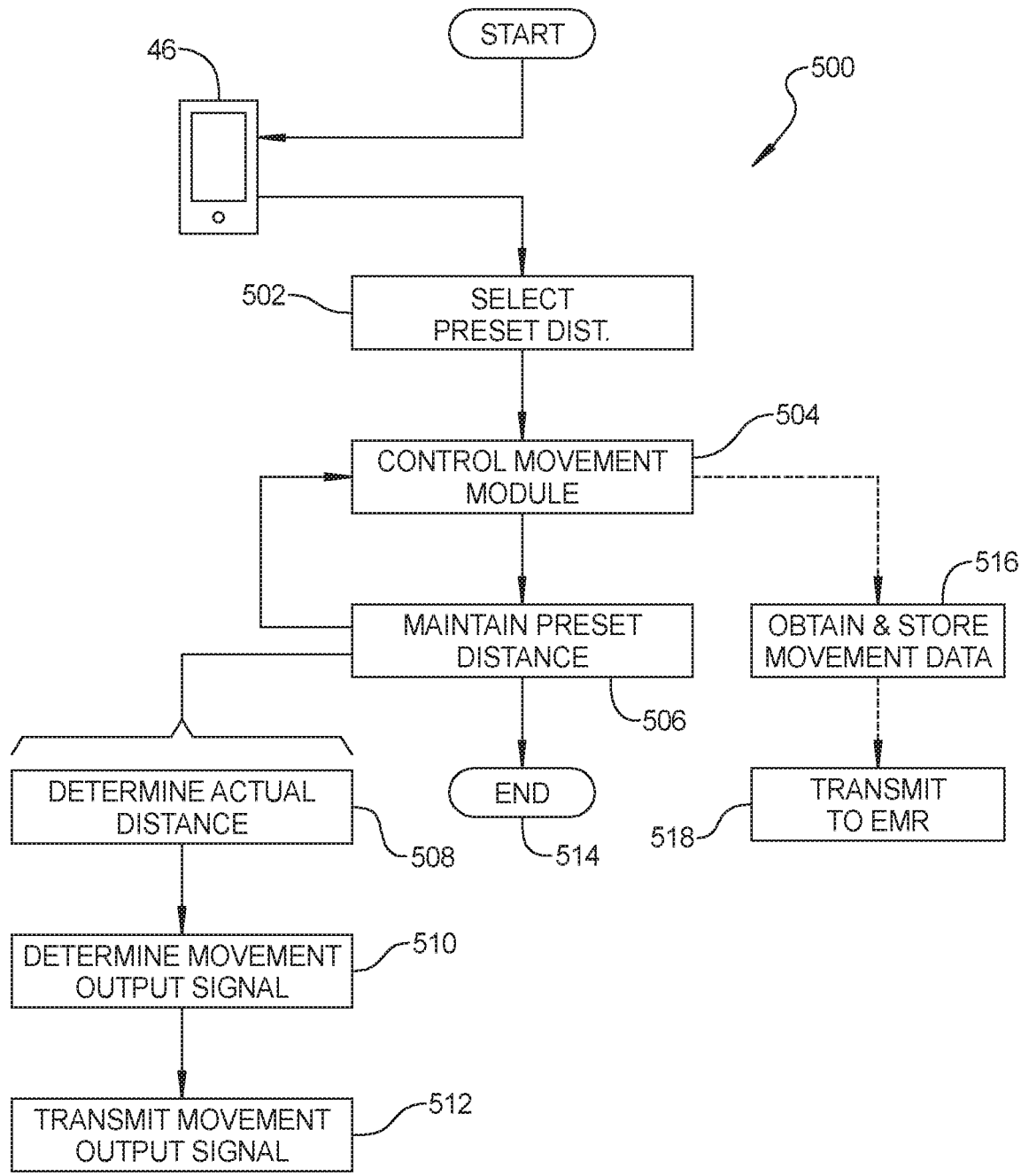
FIG. 11 is a schematic diagram detailing another exemplary operation of the autonomous accessory support systems in accordance with certain embodiments of the present disclosure.

Another exemplary method 500 for operating the autonomous accessory support 24 and/or system 20, 20', 20" is illustrated in FIG. 11. The method 500 comprises the step of selecting the preset distance (step 502). The preset distance is typically selected on the user device 46. In one example, the preset distance is a quantity with units of feet, meters, etc. In instances where the medical accessory 26a-26e is coupled to the patient 22 with the medical line 28a-28e, the preset distances is set to be smaller than or less than the length of the medical line 28a-28e. In another instance where the medical accessory 26a-26e is yet to be coupled to the patient 22, the preset distance may be greater than, less than, or equal to the length of the medical line 28. For example, the medical line 28a-28e of two to three feet may be associated with a preset distance of one foot. Often, the preset distance is less than three meters to avoid intervening obstacles as the autonomous accessory support 24 follows the patient 22.

After the preset distance is selected by the user, the controller 52 controls the movement module 32 (step 504). The controller 52 controls the movement module 32 based on the tracking input signal received from the tracking module 58. The tracking module 58 tracks the movement of the patient 22 or the patient support apparatus 100 relative to the autonomous accessory support 24 to provide the tracking input signal. The tracking input signal may be generated in part by the tracking sensor 62 on the autonomous accessory support 24 (or by the locator network 302 of the medical facility 300) detecting the tracking device 60a, 60b on the patient 22 and/or the patient support apparatus 100.

The controller 52 controlling the movement module 32 comprises maintaining the preset distance between the patient 22 and the medical accessory 26a-26e (step 506). To do so, the controller 52 may determine an actual distance (step 508), if the actual distance does or does not equal the preset distance, and the appropriate movement output signal to equalize the actual distance and the preset distance (step 510). If the controller 52 determines the movement output signal, then the controller 52 transmits the movement output signal to the movement module 32 (step 512). The steps of controlling the movement module 32 (step 504) and maintaining the preset distance (step 506) may repeat in a continuous loop until the autonomous accessory support 24 is no longer tracking the movement of the patient 22 or the patient support apparatus 100, after which the method 500 ends (step 514). The continuous feedback loop may include filtering and smoothing algorithms to prevent "jerkiness" of the movement module 32 about the preset distance. As with the exemplary method 400 of FIG. 10, the method 500 of FIG. 11 may further comprise the steps of obtaining and storing movement data in the memory device 90 (step 516), and transmitting the movement data to the patient EMR 92 (step 518).

Several embodiments have been discussed in the foregoing description. However, the embodiments discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

What is claimed is:

1. An autonomous accessory support system for transporting a medical accessory for delivering therapy that is coupled to a patient via a medical line, said autonomous accessory support system comprising:
    an autonomous accessory support comprising:
        an accessory post for supporting the medical accessory;
        a movement module supporting said accessory post for moving said accessory post relative to the patient;
        a tracking module configured to track movement of the patient or a patient support apparatus relative to said autonomous accessory support and provide a tracking input signal; and
        a controller in electronic communication with said movement module and said tracking module, said controller is configured to:
            determine a target patient proximity, said target patient proximity is a distance between said autonomous accessory support and the patient or between said autonomous accessory support and the patient support apparatus, wherein said target patient proximity is less than a length of the medical line such that tensioning of the medical line beyond a tension threshold is prevented;
            determine an actual patient proximity based on said tracking input signal;
            determine a movement output signal based on said target patient proximity and said actual patient proximity; and
            transmit said movement output signal to said movement module to reduce said actual patient proximity to said target patient proximity.

2. The autonomous accessory support system of claim 1, wherein said autonomous accessory support further comprises a rechargeable power supply coupled to said movement module.

3. The autonomous accessory support system of claim 2, further comprising an accessory port coupled to said accessory post, said accessory port being in electrical communication with said rechargeable power supply, wherein said accessory port is configured to supply power to the medical accessory.

4. The autonomous accessory support system of claim 2, wherein the movement module further comprises an ultraviolet device coupled to said rechargeable power supply and configured to disinfect a floor surface during movement of said autonomous accessory support.

5. The autonomous accessory support system of claim 2, further comprising a docking station, said docking station comprising a docking port, and wherein said rechargeable power supply comprises a charging port, said docking port configured to removably couple and supply power to said charging port of said autonomous accessory support.

6. The autonomous accessory support system of claim 5, further comprising a base connector rotatably coupled to said movement module with said charging port coupled to said base connector, wherein said base connector is configured to rotate relative to said accessory post to facilitate alignment of said charging port with said docking port during docking of said autonomous accessory support with said docking station.

7. The autonomous accessory support system of claim 5, further comprising a base connector coupled to said movement module with said charging port comprises a conductive plate disposed about at least a circumference of said base connector, wherein said docking port further comprises a terminal configured to engage said conductive plate during docking of said autonomous accessory support with said docking station regardless of orientation of said autonomous accessory support relative to said docking station.

8. The autonomous accessory support system of claim 5, wherein said docking station comprises a docking position module in electronic communication with said controller of said autonomous accessory support, said docking position module providing a docking position signal to said controller, wherein said controller is configured to:
    determine a second movement output signal based on said docking position signal; and
    transmit said second movement output signal to said movement module such that said autonomous accessory support autonomously moves to a docking position where said charging port of said autonomous accessory support engages said docking port.

9. The autonomous accessory support system of claim 8, further comprising:
    a user input device configured to provide a user input signal to said controller,
    wherein said controller is configured to transmit said second movement output signal to said movement module based on said user input signal such that said autonomous accessory support autonomously moves to said docking position.

10. The autonomous accessory support system of claim 8, said controller is further configured to determine a period of inactivity of said autonomous accessory support based on an activity input signal,
    wherein, based on said activity input signal, said controller is configured to transmit said second movement output signal to said movement module such that said autonomous accessory support autonomously moves to said docking position and couples said charging port and said docking port.

11. The autonomous accessory support system of claim 10, wherein said period of inactivity comprises a period of time during which power is not being supplied to the medical accessory.

12. The autonomous accessory support system of claim 1, wherein said autonomous accessory support further comprises a memory device in electronic communication with said controller, said controller is further configured to store movement data associated with said movement module on said memory device, said movement data comprising at least one of distance, speed, and path traveled by said movement module and indicative of an early mobility state of a patient.

13. The autonomous accessory support system of claim 12, wherein said controller is further configured to transmit said movement data to an electronic medical record.

14. The autonomous accessory support system of claim 1, wherein said accessory post comprises a bottom portion, said autonomous accessory support system further comprising a support frame coupled to said bottom portion of said accessory post, said support frame configured to be removably coupled to and supported by said movement module.

15. The autonomous accessory support system of claim 1, further comprising:
a tracking device configured to be coupled to the patient or the patient support apparatus, wherein said tracking module is configured to detect a position of said tracking device and provide said tracking input signal based on said position of said tracking device.

16. The autonomous accessory support system of claim 1, further comprising:
a tracking device configured to be coupled to the patient or the patient support apparatus,
wherein said controller is configured to receive a first location input signal and a second location input signal from a locator network within a medical facility, said first location input signal based on a location of said tracking device, and said second location input signal based on a location of said tracking module, and
wherein said tracking module is configured to determine said tracking input signal based on said first location input signal and said second location input signal.

17. The autonomous accessory support system of claim 1, further comprising said patient support apparatus.

18. A system for transporting a medical accessory coupled to a patient with a medical line, said system comprising:
a patient support apparatus configured to transport and support the patient coupled to the medical accessory via the medical line;
an autonomous accessory support comprising:
an accessory post for supporting the medical accessory;
a movement module supporting said accessory post for moving said accessory post relative to the patient;
a tracking module configured to track movement of the patient or said patient support apparatus relative to said autonomous accessory support and provide a tracking input signal; and
a controller in electronic communication with said movement module and said tracking module, said controller is configured to control said movement module based on said tracking input signal received from said tracking module to maintain a preset distance between said patient support apparatus and said medical accessory, wherein said preset distance is based on a length of the medical line such that tensioning of the medical line beyond a tension threshold is prevented.

19. The system of claim 18, further comprising a user input device configured to provide a user input signal to said controller, said controller configured to adjust said preset distance based on said user input signal.

20. An autonomous accessory support for transporting a medical accessory for delivering therapy that is coupled to a patient via a medical line at a patient site, said autonomous accessory support comprising:
an accessory post for supporting said medical accessory;
a movement module supporting said accessory post for moving said accessory post relative to the patient;
a tracking module configured to track movement of the patient relative to said autonomous accessory support and provide a tracking input signal; and
a controller in electronic communication with said movement module and said tracking module, said controller is configured to control said movement module based on said tracking input signal received from said tracking module to maintain a preset distance between the patient and said medical accessory, wherein said preset distance is based on a length of the medical line such that tensioning of the medical line beyond a tension threshold is prevented.

21. The autonomous accessory support of claim 20, wherein said preset distance is selectable by a user to prevent tensioning of the medical line at the patient site.

* * * * *